US011383076B2

(12) United States Patent
Anstadt

(10) Patent No.: US 11,383,076 B2
(45) Date of Patent: Jul. 12, 2022

(54) PUMP REGULATION BASED ON HEART SIZE AND FUNCTION

(71) Applicant: LifeBridge Technologies, LLC, Dayton, OH (US)

(72) Inventor: Mark P. Anstadt, Kettering, OH (US)

(73) Assignee: LifeBridge Technologies, LLC, Dayton, OH (US)

( * ) Notice: Subject to any disclaimer, the term of this patent is extended or adjusted under 35 U.S.C. 154(b) by 0 days.

(21) Appl. No.: 17/208,776

(22) Filed: Mar. 22, 2021

(65) Prior Publication Data
US 2022/0105338 A1     Apr. 7, 2022

Related U.S. Application Data

(60) Provisional application No. 63/086,478, filed on Oct. 1, 2020.

(51) Int. Cl.
| | | |
|---|---|---|
| *A61M 60/00* | (2021.01) | |
| *A61M 60/538* | (2021.01) | |
| *A61M 60/569* | (2021.01) | |
| *A61M 60/117* | (2021.01) | |
| *A61M 60/432* | (2021.01) | |
| A61M 60/268 | (2021.01) | |
| A61M 60/40 | (2021.01) | |

(52) U.S. Cl.
CPC ........ *A61M 60/538* (2021.01); *A61M 60/117* (2021.01); *A61M 60/432* (2021.01); *A61M 60/569* (2021.01); A61M 60/00 (2021.01); A61M 60/268 (2021.01); A61M 60/40 (2021.01); A61M 2205/50 (2013.01)

(58) Field of Classification Search
CPC .............. A61M 60/538; A61M 60/117; A61M 60/432; A61M 60/569; A61M 2205/50; A61M 60/00; A61M 60/268; A61M 60/40
See application file for complete search history.

(56) References Cited

U.S. PATENT DOCUMENTS

| | | |
|---|---|---|
| 2,826,193 A | 3/1958 | Vineberg |
| 2,889,780 A | 6/1959 | Binford |
| 3,053,249 A | 9/1962 | Smith |
| (Continued) | | |

OTHER PUBLICATIONS

International Search Report and Written Opinion of International Application No. PCT/US2021/53231 dated Dec. 22, 2021, 15 pages.

*Primary Examiner* — Michael W Kahelin
*Assistant Examiner* — Pamela M. Bays
(74) *Attorney, Agent, or Firm* — Lowenstein Sandler LLP; Madhumita Datta

(57) ABSTRACT

Disclosed are techniques to generate ideal or near ideal profiles for regulation of the volume of fluid flow in a drive system of a pump for an externally mechanically supported heart, pressure in or near the pump, or measured strain/strain rates of the supported heart, based on an estimate/measurement of the heart's size. A part of the techniques for regulation may focus on achieving mechanical synchrony with the intrinsic cyclic pump function of a partially functional heart. The techniques do not fundamentally rely on hemodynamic measurements to function. However, when hemodynamic measures are available, those measures can be fed to control algorithms to increase the efficacy of regulation to restore the heart's pump function.

16 Claims, 23 Drawing Sheets

(56) References Cited

U.S. PATENT DOCUMENTS

| | | |
|---|---|---|
| 3,233,607 A | 2/1966 | Bolie |
| 3,279,464 A | 10/1966 | Check |
| 3,304,501 A | 2/1967 | Ruthenberg |
| 3,371,662 A | 3/1968 | Heid |
| 3,376,863 A | 4/1968 | Kolobow |
| 3,449,767 A | 6/1969 | Bolie |
| 3,455,298 A | 7/1969 | Anstadt |
| 3,478,737 A | 11/1969 | Rassman |
| 3,513,836 A | 5/1970 | Sausse |
| 3,587,567 A | 6/1971 | Schiff |
| 3,590,815 A | 7/1971 | Shiff |
| 3,613,672 A | 10/1971 | Schiff |
| 3,674,381 A | 7/1972 | Schiff |
| 4,048,990 A | 9/1977 | Goetz |
| 4,192,293 A | 3/1980 | Asrican |
| 4,281,669 A | 8/1981 | MacGregor |
| 4,448,190 A | 5/1984 | Freeman |
| 4,536,893 A | 8/1985 | Parravicini |
| 4,609,176 A | 9/1986 | Powers |
| 4,621,617 A | 11/1986 | Sharma |
| 4,662,358 A | 5/1987 | Farrar |
| 4,684,143 A | 8/1987 | Sato |
| 4,957,477 A | 9/1990 | Lundback |
| 4,979,936 A | 12/1990 | Stephenson |
| 5,006,111 A | 4/1991 | Inokuchi |
| 5,089,017 A | 2/1992 | Young |
| 5,098,369 A | 3/1992 | Heilman et al. |
| 5,098,442 A | 3/1992 | Grandjean |
| 5,119,804 A | 6/1992 | Anstadt |
| 5,131,905 A | 7/1992 | Grooters |
| 5,156,154 A | 10/1992 | Valenta, Jr. et al. |
| 5,158,978 A | 10/1992 | Rubin |
| 5,169,381 A | 12/1992 | Snyders |
| 5,199,804 A | 4/1993 | Rimbey et al. |
| 5,205,722 A | 4/1993 | Hammond |
| 5,256,132 A | 10/1993 | Snyders |
| 5,273,518 A | 12/1993 | Lee et al. |
| 5,322,067 A * | 6/1994 | Prater .................... A61B 8/08 128/916 |
| 5,330,505 A | 7/1994 | Cohen |
| 5,364,337 A | 11/1994 | Guiraudon et al. |
| 5,368,451 A | 11/1994 | Hammond |
| 5,374,287 A | 12/1994 | Rubin |
| 5,383,840 A | 1/1995 | Heilman et al. |
| 5,385,528 A | 1/1995 | Wilk |
| 5,429,584 A | 7/1995 | Chiu |
| 5,476,502 A | 12/1995 | Rubin |
| 5,496,353 A | 3/1996 | Grandjean et al. |
| 5,533,958 A | 7/1996 | Wilk |
| 5,558,617 A | 9/1996 | Heilman et al. |
| 5,562,595 A | 10/1996 | Neisz |
| 5,658,237 A | 8/1997 | Francischelli |
| 5,674,259 A | 10/1997 | Gray |
| 5,697,884 A | 12/1997 | Francischelli et al. |
| 5,697,952 A | 12/1997 | Francischelli et al. |
| 5,707,336 A | 1/1998 | Rubin |
| 5,713,954 A | 2/1998 | Rosenberg et al. |
| 5,716,379 A | 2/1998 | Bourgeois et al. |
| 5,738,627 A | 4/1998 | Kovacs et al. |
| 5,749,839 A | 5/1998 | Kovacs |
| 5,769,800 A | 6/1998 | Gelfand et al. |
| 5,800,334 A | 9/1998 | Wilk |
| 5,861,558 A | 1/1999 | Buhl et al. |
| 5,876,345 A | 3/1999 | Eaton et al. |
| 5,902,229 A | 5/1999 | Tsitlik et al. |
| 5,908,378 A | 6/1999 | Kovacs et al. |
| 5,910,124 A | 6/1999 | Rubin |
| 5,919,209 A | 7/1999 | Schouten |
| 5,971,910 A | 10/1999 | Tsitlik et al. |
| 5,971,911 A | 10/1999 | Wilk |
| 5,980,571 A | 11/1999 | Nomura et al. |
| 6,042,532 A | 3/2000 | Freed et al. |
| 6,044,298 A | 3/2000 | Salo et al. |
| 6,059,750 A | 5/2000 | Fogarty et al. |
| 6,076,013 A | 6/2000 | Brennan et al. |
| 6,095,968 A | 8/2000 | Snyders |
| 6,110,098 A | 8/2000 | Renirie et al. |
| 6,123,726 A | 9/2000 | Mori et al. |
| 6,132,363 A | 10/2000 | Freed et al. |
| 6,183,412 B1 | 2/2001 | Benkowski et al. |
| 6,206,820 B1 | 3/2001 | Kazi et al. |
| 6,238,334 B1 | 5/2001 | Easterbrook, III et al. |
| 6,251,061 B1 | 6/2001 | Hastings et al. |
| 6,254,525 B1 | 7/2001 | Reinhardt et al. |
| 6,282,445 B1 | 8/2001 | Reinhardt et al. |
| 6,298,266 B1 | 10/2001 | Rubin et al. |
| 6,309,380 B1 | 10/2001 | Larson et al. |
| 6,328,689 B1 | 12/2001 | Gonzalez et al. |
| 6,408,205 B1 | 6/2002 | Renirie et al. |
| 6,432,039 B1 | 8/2002 | Wardle |
| 6,438,411 B1 | 8/2002 | Guttman et al. |
| 6,464,655 B1 | 10/2002 | Shahinpoor |
| 6,485,407 B2 | 11/2002 | Alferness et al. |
| 6,508,756 B1 | 1/2003 | Kung et al. |
| 6,540,659 B1 | 4/2003 | Milbocker |
| 6,547,716 B1 | 4/2003 | Milbocker |
| 6,572,534 B1 | 6/2003 | Milbocker et al. |
| 6,602,182 B1 | 8/2003 | Milbocker |
| 6,612,978 B2 | 9/2003 | Lau et al. |
| 6,616,596 B1 | 9/2003 | Milbocker |
| 6,622,045 B2 | 9/2003 | Snell et al. |
| 6,626,821 B1 | 9/2003 | Kung et al. |
| 6,641,604 B1 | 11/2003 | Adelman et al. |
| 6,682,474 B2 | 1/2004 | Lau et al. |
| 6,730,016 B1 | 5/2004 | Cox et al. |
| 6,757,561 B2 | 6/2004 | Rubin et al. |
| 6,808,483 B1 | 10/2004 | Ortiz et al. |
| 6,846,296 B1 | 1/2005 | Milbocker et al. |
| 6,971,127 B2 | 12/2005 | Richards |
| 7,331,221 B2 | 2/2008 | Wise et al. |
| 7,494,459 B2 | 2/2009 | Anstadt et al. |
| 7,871,366 B2 | 1/2011 | Criscione et al. |
| 8,187,160 B2 | 5/2012 | Criscione et al. |
| 2003/0032855 A1* | 2/2003 | Shahinpoor ......... A61M 60/268 600/16 |
| 2004/0010180 A1 | 1/2004 | Scorvo |
| 2004/0024315 A1* | 2/2004 | Chalana ............... A61B 8/0858 600/443 |
| 2004/0059183 A1 | 3/2004 | Jansen |
| 2004/0078067 A1 | 4/2004 | Thompson et al. |
| 2004/0102674 A1 | 5/2004 | Zadini et al. |
| 2004/0116769 A1 | 6/2004 | Jassawalla |
| 2004/0167375 A1 | 8/2004 | Couvillon |
| 2004/0225177 A1 | 11/2004 | Coleman et al. |
| 2004/0267086 A1 | 12/2004 | Anstadt et al. |
| 2005/0113632 A1 | 5/2005 | Ortiz et al. |
| 2005/0148814 A1 | 7/2005 | Fischi et al. |
| 2005/0234289 A1 | 10/2005 | Anstadt et al. |
| 2006/0142634 A1 | 6/2006 | Anstadt et al. |
| 2006/0167334 A1 | 7/2006 | Anstadt et al. |
| 2006/0211909 A1 | 9/2006 | Anstadt et al. |
| 2007/0078489 A1 | 4/2007 | Meyer et al. |
| 2008/0257412 A1 | 10/2008 | Gordon |
| 2010/0152523 A1 | 6/2010 | MacDonald et al. |
| 2011/0196189 A1 | 8/2011 | Milbocker |
| 2016/0101230 A1* | 4/2016 | Ochsner ............... A61B 5/1073 600/17 |
| 2019/0224395 A1 | 7/2019 | Pilla et al. |

* cited by examiner

Table 1

| Maximal Cardiac Volume During Device Support ||
| Diameter$_{(ED)}$ mm | Volume at end-diastole |
| --- | --- |
| 35 ± 4 | 15 ± 1.5 |
| 40 ± 4 | 22 ± 2.2 |
| 45 ± 4 | 34 ± 3.4 |
| 50 ± 4 | 50 ± 5.0 |
| 55 ± 4 | 75 ± 7.5 |
| 60 ± 4 | 100 ± 10 |
| 65 ± 4 | 140 ± 14 |
| 70 ± 4 | 180 ± 18 |
| 75 ± 4 | 220 ± 22 |
| 80 ± 4 | 270 ± 27 |
| 85 ± 4 | 330 ± 33 |
| 90 ± 4 | 400 ± 40 |
| 95 ± 4 | 460 ± 46 |
| 100 ± 4 | 530 ± 53 |
| 105 ± 4 | 600 ± 60 |
| 110 ± 4 | 700 ± 70 |
| 115 ± 4 | 800 ± 80 |
| 120 ± 4 | 900 ± 90 |
| 125 ± 4 | 1000 ± 100 |
| 130 ± 4 | 1100 ± 110 |
| 135 ± 4 | 1200 ± 120 |
| 140 ± 4 | 1300 ± 130 |

Table 2

Target Actuation Mode Settings

| $D_{(ED)}$ (mm) | Volume Delivery (V) (cc) | Rate ($f$) (bpm) |
|---|---|---|
| 35 ± 4 | 12 ± 2 | 170 ± 20 |
| 40 ± 4 | 20 ± 2 | 160 ± 10 |
| 45 ± 4 | 50 ± 5 | 155 ± 10 |
| 50 ± 4 | 100 ± 10 | 150 ± 10 |
| 55 ± 4 | 170 ± 17 | 145 ± 10 |
| 60 ± 4 | 250 ± 25 | 140 ± 10 |
| 65 ± 4 | 340 ± 34 | 135 ± 10 |
| 70 ± 4 | 500 ± 50 | 130 ± 10 |
| 75 ± 4 | 620 ± 62 | 125 ± 10 |
| 80 ± 4 | 740 ± 74 | 115 ± 10 |
| 85 ± 4 | 870 ± 87 | 110 ± 10 |
| 90 ± 4 | 990 ± 99 | 105 ± 10 |
| 95 ± 4 | 1110 ± 110 | 95 ± 10 |
| 100 ± 4 | 1240 ± 124 | 90 ± 10 |
| 105 ± 4 | 1360 ± 136 | 85 ± 5 |
| 110 ± 4 | 1480 ± 148 | 80 ± 5 |
| 115 ± 4 | 1600 ± 160 | 75 ± 5 |
| 120 ± 4 | 1730 ± 173 | 70 ± 5 |
| 125 ± 4 | 1850 ± 185 | 65 ± 5 |
| 130 ± 4 | 1980 ± 198 | 60 ± 5 |
| 135 ± 4 | 2100 ± 210 | 55 ± 5 |
| 140 ± 4 | 2270 ± 227 | 50 ± 5 |

FIG. 9

Table 3

Target Assist Mode Settings

| $D_{(ED)}$ (mm) | Volume Delivery (V) (cc) | Rate ($f$) (bpm) |
|---|---|---|
| 35 ± 4 | 12 ± 2 | 180 ± 20 |
| 40 ± 4 | 20 ± 2 | 170 ± 10 |
| 45 ± 4 | 50 ± 5 | 165 ± 10 |
| 50 ± 4 | 100 ± 10 | 160 ± 10 |
| 55 ± 4 | 170 ± 17 | 155 ± 10 |
| 60 ± 4 | 250 ± 25 | 150 ± 10 |
| 65 ± 4 | 340 ± 34 | 145 ± 10 |
| 70 ± 4 | 500 ± 50 | 140 ± 10 |
| 75 ± 4 | 620 ± 62 | 135 ± 10 |
| 80 ± 4 | 740 ± 74 | 125 ± 10 |
| 85 ± 4 | 870 ± 87 | 120 ± 10 |
| 90 ± 4 | 990 ± 99 | 115 ± 10 |
| 95 ± 4 | 1110 ± 110 | 105 ± 10 |
| 100 ± 4 | 1240 ± 124 | 100 ± 10 |
| 105 ± 4 | 1360 ± 136 | 90 ± 5 |
| 110 ± 4 | 1480 ± 148 | 85 ± 5 |
| 115 ± 4 | 1600 ± 160 | 80 ± 5 |
| 120 ± 4 | 1730 ± 173 | 75 ± 5 |
| 125 ± 4 | 1850 ± 185 | 70 ± 5 |
| 130 ± 4 | 1980 ± 198 | 65 ± 5 |
| 135 ± 4 | 2100 ± 210 | 60 ± 5 |
| 140 ± 4 | 2270 ± 227 | 55 ± 5 |

FIG. 12

Table 4

| $D_{(ED)}$ (mm) | $A_{max}$ (mm Hg) | $A_{min}$ (mm Hg) | $f$ (bps) |
|---|---|---|---|
| Target Pressure Actuation Settings ||||
| 35 ± 4 | 178 ± 27 | -75 ± 32 | 2.83 ± 0.26 |
| 40 ± 4 | 174 ± 26 | -72 ± 31 | 2.67 ± 0.17 |
| 45 ± 4 | 170 ± 25 | -70 ± 30 | 2.58 ± 0.17 |
| 50 ± 4 | 166 ± 24 | -68 ± 29 | 2.50 ± 0.17 |
| 55 ± 4 | 163 ± 23 | -66 ± 28 | 2.42 ± 0.17 |
| 60 ± 4 | 159 ± 22 | -64 ± 27 | 2.33 ± 0.17 |
| 65 ± 4 | 155 ± 21 | -62 ± 26 | 2.25 ± 0.17 |
| 70 ± 4 | 152 ± 20 | -60 ± 25 | 2.17 ± 0.17 |
| 75 ± 4 | 148 ± 18 | -58 ± 24 | 2.08 ± 0.17 |
| 80 ± 4 | 144 ± 17 | -56 ± 23 | 1.92 ± 0.17 |
| 85 ± 4 | 141 ± 16 | -54 ± 22 | 1.83 ± 0.17 |
| 90 ± 4 | 137 ± 15 | -52 ± 21 | 1.75 ± 0.17 |
| 95 ± 4 | 133 ± 14 | -50 ± 20 | 1.58 ± 0.17 |
| 100 ± 4 | 130 ± 13 | -48 ± 19 | 1.50 ± 0.17 |
| 105 ± 4 | 126 ± 12 | -46 ± 18 | 1.42 ± 0.08 |
| 110 ± 4 | 122 ± 11 | -44 ± 17 | 1.33 ± 0.08 |
| 115 ± 4 | 118 ± 10 | -42 ± 16 | 1.25 ± 0.08 |
| 120 ± 4 | 115 ± 9 | -40 ± 15 | 1.17 ± 0.08 |
| 125 ± 4 | 111 ± 8 | -38 ± 14 | 1.08 ± 0.08 |
| 130 ± 4 | 108 ± 7 | -36 ± 13 | 1.00 ± 0.08 |
| 135 ± 4 | 104 ± 6 | -33 ± 12 | 0.92 ± 0.08 |
| 140 ± 4 | 100 ± 5 | -30 ± 10 | 0.83 ± 0.08 |

FIG. 16

Table 5

| $D_{(ED)}$ (mm) | $A_{max}$ (mm Hg) | $A_{min}$ (mm Hg) | $f$ (bps) |
|---|---|---|---|
| 35 ± 4 | 188 ± 27 | -75 ± 32 | 3.00 ± 0.26 |
| 40 ± 4 | 182 ± 26 | -72 ± 31 | 2.83 ± 0.17 |
| 45 ± 4 | 176 ± 25 | -70 ± 30 | 2.75 ± 0.17 |
| 50 ± 4 | 170 ± 24 | -68 ± 29 | 2.67 ± 0.17 |
| 55 ± 4 | 164 ± 23 | -66 ± 28 | 2.58 ± 0.17 |
| 60 ± 4 | 158 ± 22 | -64 ± 27 | 2.50 ± 0.17 |
| 65 ± 4 | 152 ± 21 | -62 ± 26 | 2.42 ± 0.17 |
| 70 ± 4 | 146 ± 20 | -60 ± 25 | 2.33 ± 0.17 |
| 75 ± 4 | 140 ± 18 | -58 ± 24 | 2.25 ± 0.17 |
| 80 ± 4 | 134 ± 17 | -56 ± 23 | 2.08 ± 0.17 |
| 85 ± 4 | 128 ± 16 | -54 ± 22 | 2.00 ± 0.17 |
| 90 ± 4 | 122 ± 15 | -52 ± 21 | 1.92 ± 0.17 |
| 95 ± 4 | 116 ± 14 | -50 ± 20 | 1.75 ± 0.17 |
| 100 ± 4 | 110 ± 13 | -48 ± 19 | 1.67 ± 0.17 |
| 105 ± 4 | 104 ± 12 | -46 ± 18 | 1.50 ± 0.08 |
| 110 ± 4 | 98 ± 11 | -44 ± 17 | 1.42 ± 0.08 |
| 115 ± 4 | 92 ± 10 | -42 ± 16 | 1.33 ± 0.08 |
| 120 ± 4 | 86 ± 9 | -40 ± 15 | 1.25 ± 0.08 |
| 125 ± 4 | 80 ± 8 | -38 ± 14 | 1.17 ± 0.08 |
| 130 ± 4 | 74 ± 7 | -36 ± 13 | 1.08 ± 0.08 |
| 135 ± 4 | 68 ± 6 | -33 ± 12 | 1.00 ± 0.08 |
| 140 ± 4 | 62 ± 5 | -30 ± 10 | 0.92 ± 0.08 |

FIG. 19

Table 7

Table 7 - Strain Rate Parameters

| $D_{(ED)}$ (mm) | Strain Rate Peak Magnitude ($\dot{\varepsilon}_{max}$) (1/s) | Actuation Rate ($f$) (bpm) |
|---|---|---|
| 35 ± 4 | 2.68 ± 0.21 | 180 ± 20 |
| 40 ± 4 | 2.51 ± 0.20 | 170 ± 10 |
| 45 ± 4 | 2.37 ± 0.19 | 165 ± 10 |
| 50 ± 4 | 2.24 ± 0.18 | 160 ± 10 |
| 55 ± 4 | 2.13 ± 0.17 | 155 ± 10 |
| 60 ± 4 | 2.02 ± 0.16 | 150 ± 10 |
| 65 ± 4 | 1.92 ± 0.15 | 145 ± 10 |
| 70 ± 4 | 1.83 ± 0.15 | 140 ± 10 |
| 75 ± 4 | 1.75 ± 0.14 | 135 ± 10 |
| 80 ± 4 | 1.67 ± 0.13 | 125 ± 10 |
| 85 ± 4 | 1.6 ± 0.13 | 120 ± 10 |
| 90 ± 4 | 1.53 ± 0.12 | 115 ± 10 |
| 95 ± 4 | 1.46 ± 0.12 | 105 ± 10 |
| 100 ± 4 | 1.40 ± 0.11 | 100 ± 10 |
| 105 ± 4 | 1.34 ± 0.11 | 90 ± 5 |
| 110 ± 4 | 1.28 ± 0.10 | 85 ± 5 |
| 115 ± 4 | 1.23 ± 0.09 | 80 ± 5 |
| 120 ± 4 | 1.18 ± 0.09 | 75 ± 5 |
| 125 ± 4 | 1.13 ± 0.09 | 70 ± 5 |
| 130 ± 4 | 1.08 ± 0.09 | 65 ± 5 |
| 135 ± 4 | 1.04 ± 0.08 | 60 ± 5 |
| 140 ± 4 | 0.99 ± 0.08 | 55 ± 5 |

FIG. 29

Table 6

Table 6 - Strain Parameters

| $D_{(ED)}$ (mm) | Strain Magnitude ($\varepsilon_{max}$) (%) | Actuation Rate ($f$) (bpm) |
|---|---|---|
| 35 ± 4 | 12.1 ± 0.8 | 180 ± 20 |
| 40 ± 4 | 12.8 ± 0.9 | 170 ± 10 |
| 45 ± 4 | 13.4 ± 0.9 | 165 ± 10 |
| 50 ± 4 | 14.0 ± 1.0 | 160 ± 10 |
| 55 ± 4 | 14.6 ± 1.0 | 155 ± 10 |
| 60 ± 4 | 15.3 ± 1.1 | 150 ± 10 |
| 65 ± 4 | 15.9 ± 1.1 | 145 ± 10 |
| 70 ± 4 | 16.5 ± 1.2 | 140 ± 10 |
| 75 ± 4 | 17.1 ± 1.2 | 135 ± 10 |
| 80 ± 4 | 17.8 ± 1.2 | 125 ± 10 |
| 85 ± 4 | 18.4 ± 1.3 | 120 ± 10 |
| 90 ± 4 | 19.0 ± 1.3 | 115 ± 10 |
| 95 ± 4 | 19.6 ± 1.4 | 105 ± 10 |
| 100 ± 4 | 20.2 ± 1.4 | 100 ± 10 |
| 105 ± 4 | 20.9 ± 1.5 | 90 ± 5 |
| 110 ± 4 | 21.5 ± 1.5 | 85 ± 5 |
| 115 ± 4 | 22.1 ± 1.5 | 80 ± 5 |
| 120 ± 4 | 22.7 ± 1.6 | 75 ± 5 |
| 125 ± 4 | 23.4 ± 1.6 | 70 ± 5 |
| 130 ± 4 | 24.0 ± 1.7 | 65 ± 5 |
| 135 ± 4 | 24.6 ± 1.7 | 60 ± 5 |
| 140 ± 4 | 25.2 ± 1.8 | 55 ± 5 |

FIG. 22

D = drive system pressure peak
H = heart signal peak

PUMP REGULATION BASED ON HEART SIZE AND FUNCTION

RELATED APPLICATION

This application claims the benefit of U.S. Provisional Patent Application No. 63/086,478, filed Oct. 1, 2020, entitled, "Algorithmically-Regulated Drive for Mechanical Support Device for Heart," the entirety of which is incorporated by reference herein.

TECHNICAL FIELD

The present disclosure relates to controlling effective functioning of a drive system coupled to a device that is configured to mechanically support an arrested, failing or malfunctioning heart based on the heart's size.

BACKGROUND

A variety of cardiac support devices (also referred to as "cardiac pump devices" or simply a "pump" in the specification and the subsequent claims) function by imparting an external force to the outer surface of an arrested or failing heart from the outside in an effort to eventually restore the physiologic function of the heart. A number of terms have be used to describe these devices and their methods of functioning. The terms include, but are not limited to, Direct Cardiac Compression (DCC), Cardiac Actuation, Cardiac Massage, Mechanical Cardiac Compression Device, Mechanical Cardiac Massage etc. The distinction between the variety of devices used to mechanically pump the heart can be subtle in some regards, such as shape, material construct of components acting on the heart, and means for powering their function. Most of these devices focus on aiding at least some component of the heart's (or a specific heart chamber's, such as left or right ventricle's) pump function. These cardiac support devices are somewhat similar to each other in that all of them exert mechanical forces onto the heart's surface. However they vary in their functionalities that involve either primarily compressing the heart and thereby aiding more in systolic pump function (i.e. the process of emptying the heart), or, primarily expanding the heart and thereby aiding more in diastolic pump function (i.e., the process of filling the heart for the next contraction). Some methods provide both diastolic pump function and systolic pump function. The present inventor identified a need for designing a versatile drive system control that can work in conjunction with any cardiac support device based on an estimate/measurement of the heart's size being supported.

Most existing cardiac support devices generally rely on feedback from the hemodynamic results they achieve, which are used to adjust control of the devices' action on the heart. The control in this fashion is based on the hemodynamic response of the circulatory system. This existing type of control is non-intuitive and can result in inappropriate assumptions regarding device function being coupled to understandable circulatory system responses. Furthermore, cardiovascular measures are frequently unavailable during emergency application in life-threatening circumstances.

There is a clear need to design a drive system control which is capable of operation, at least in the beginning before heart's native function is partially restored, without any hemodynamic feedback. This disclosure describes a novel drive system control that can operate without hemodynamic feedback, as well as can improve the operation whether or not hemodynamic feedback is available.

SUMMARY

The following is a simplified summary of the disclosure in order to provide a basic understanding of some aspects of the disclosure. This summary is not an extensive overview of the disclosure. It is intended to neither identify key or critical elements of the disclosure, nor delineate any scope of the particular implementations of the disclosure or any scope of the claims. Its sole purpose is to present some concepts of the disclosure in a simplified form as a prelude to the more detailed description that is presented later.

The present inventor recognized that cardiac size and cardiac size change are the fundamental determinant of how externally applied mechanical forces for pumping a fully or partially dysfunctional heart are best controlled or modulated to allow the heart, in turn, to regain and/or maintain or improve its native pump function in this setting, i.e., while being supported by the device, the degree of support varying situationally. This realization led the inventor to discover that measurement of cardiac size can be utilized to derive a set of optimal drive pressure and/or drive flow profiles that could dictate how the heart can most ideally pump when acted upon by the pump. In turn, the ideal pump characteristics of the heart are exhibited by a set of strain/strain rate profiles. Thus, drive profiles of either or both of flow and pressure are generated to reliably pump the heart based on the heart's size. Furthermore, the optimal heart pump function resulting from these drive profiles can be extrapolated from a set of heart strain and/or strain rate profiles. Finally, this disclosure also describes that synchronization between the drive system's pumping action and the native contraction of the heart becomes an independent means for control if the heart is at least partially functional.

More specifically, disclosed herein are drive system controllers that rely on algorithms to periodically assess heart size (at a user-selectable frequency of re-assessment) and periodically generate ideal or near ideal profiles (also referred to as waveforms) for fluid flow in the drive system, and/or pressure in or near the pump and/or strain or strain rate of the heart resulting pump function to best regulate the heart's pump function for the corresponding heart size.

The regulation techniques fundamentally require an estimate/measurement of the heart's size to generate these profiles. The heart's size can be estimated/measured by a variety of methods known to the persons skilled in the art, for example, ultrasound. The measurement is preferably done by a non-invasive means. Common ways to estimate/measure the heart size can be based on estimating/measuring the longitudinal cross-sectional length at the base of the heart or estimating/measuring the diameter of the portion of the heart just below the atrioventricular valves where it is generally at its greatest width. The measurement/estimation is done either before or after the pump is coupled to the heart. The ideal measure is that which will correlate to the entire volume occupied by the heart during the heart end-diastolic time of cyclic pump function. Notably, this can change during cardiac support and re-estimating/re-measuring heart size during support is an important aspect of this control algorithm. Real-time measurement of change of heart size due to various phenomena, such as respiration, myocardial contraction, vascular resistance change, vascular elasticity change, intra-vascular fluid volume change, can be incorporated in the algorithm to increase the efficacy of drive control and functional support to the heart.

A first order of control of the pump is provided by matching stored target profiles for fluid flow in the drive system coupled to the pump. A second order of control is provided by matching stored target profiles for pressure at, near or within the pump.

A third order of control is provided by matching stored target profiles for strains/strain rates (e.g., left ventricular (LV) strain or LV strain rate) measured across the patient's body or from within the blood circulation. Each of the above-mentioned target profiles can be for systolic support, diastolic support, or both systolic and diastolic support. Notably, the strain/strain rate profiles provide unique means for segregating the function imposed externally by the pump from the native function that the heart itself provides at a particular time. When the pump is off, strain or strain rate profiles represent the heart's native function, assuming the heart is not completely arrested, and capable of providing some native function, albeit compromised. On the other hand, when the heart is arrested, i.e., not beating, strain/strain rate profiles strictly represent the function imparted by the pump.

A fourth order of control can be provided through an optimization algorithm called a mechanical synchrony algorithm. Mechanical synchrony aspects include periodic interrogation of the heart rate (by flow, arterial pressure, electrocardiogram (ECG), peak strain etc.). For example, mechanical synchrony algorithm aligns measures of peak systolic pressure in the drive system or the pump with physiologic measures of the heart's systolic pump function to achieve ideal systolic, or diastolic, or both systolic and diastolic support. The heart generally contracts with a regular rhythm. Although the rhythm can be irregular, it has a general average rate of contraction over increments of time. Pumps disclosed in the application provide a regular rate for heart assist or actuation (described further below). The rate is regulated by the drive system and is generally very regular over specified period of times as set by the operation of the drive. Mechanical pacing is a concept central to the fourth order of control (mechanical synchrony) that uses repeated interrogation of the heart's contraction in relation to the device's action to best align the device action to the heart's native contraction. Mechanical pacing is premised on the understanding that over time the heart's inherent contraction rate may vary and therefore, re-interrogation is performed periodically to ensure the heart and device are at optimal synchrony. In this manner the device improves the heart's pump function while reducing the chance of the heart working independently, which may put undue pressure on the heart that is not fully functional. The objective of mechanical pacing is to use the mechanical deformation of the heart during cardiac support to trigger an electrical signal that would dynamically synchronize the pump's actuation with the heart's native contractile action, as the heart is receptive to the electrical stimulus More specifically, the goal of mechanical synchrony can be three-fold: 1) improving heart's native contractile function which is already existing, though may have been severely or partially compromised; 2) improving the likelihood that the pump compresses in close proximity to the heart contraction, and 3) improving the likelihood that that mechanical stimulus of the device leads to the mechanical contraction of the heart. Like the strain/strain rate profiles discussed above, mechanical synchrony algorithm also provides a way to separate how much functionality the pump is creating from the heart's native pump functionality (which may be zero or compromised depending on the severity of dysfunction). With the pump off, the heart that is not fully arrested, may be able to independently create pulses and synchronize the pumping cycle with the intrinsic pulses. On the other hand, when the heart has no intrinsic pulses, the pump can stimulate the synchronization, and then adjust the level of external support based on how much the heart's native functions are restored.

Each of the above four orders of controls can function independent of the other orders. However, one or more of the four orders of control can also be combined to improve the efficacy of overall regulation of the drive system.

Corresponding target profiles can be utilized for an "actuation" mode (where the heart's native function is severely compromised or absent), an "assist" mode (where the heart has retained or has regained some amount of pump function), and a "weaning" mode (where the heart has adequate function, such that the pump may not be necessary but may still beneficially augment the heart's function or ability to recover). Note that the term "assist" mode can encompass the "weaning" mode also depending on how the threshold percentage of the heart's native function (compared to a baseline of 100% or normal function) is defined. Also, note that all three modes may not need all the orders of control. For example, the flow or pressure profile based control may be most effective in the "assist" and "actuation" modes, but may be not as necessary in the "weaning" mode. On the other hand, mechanical synchrony may be very effective in the "assist" and/or "weaning" modes (which can be thought of an extension of the "assist" mode), but not that much effective in the "actuation" mode. Mechanical synchrony can be effective means for control even if target profiles based on other orders of control are not available or not relied on. Instead, hemodynamic feedback can be relied on more in the "weaning" mode. Note that optionally, one of the goals in the weaning mode can be to transition the pump off a recovered heart, but augmenting the function of a partially or fully recovered heart with the help of a pump is also encompassed by the term "weaning".

The heart generally pumps blood to provide sufficient life-sustaining blood flow to the body. This patent application addresses conditions in which the body is at relatively greater need of blood flow, such as following a cardiac arrest and/or severe states of heart failure where vital organs are at risk of failure if flow cannot be adequately returned and/or maintained. Therefore, target profiles for the drive system, especially in the "actuation mode" and also in the "assist mode" are primarily directed toward maximizing pump function. In certain other situations, where the heart is providing sufficient blood flow but the addition of support aids the heart in recovery and/or maintaining its function (i.e., less severe heart failure states), target profiles can be tuned to the degree of support that are commensurate with the situation. These target profiles are termed weaning profiles or "weaning mode" of support. Generating specific profiles for the weaning mode are an extension of what is described in the "Detailed Description" section with illustrative examples, and are covered within the scope of this disclosure.

The control algorithms do not fundamentally rely on hemodynamic measurements to regulate drive system function. However, when hemodynamic measures are available, those measures can be fed to the algorithms to increase the drive system's efficacy and select the best profiles to achieve ideal pump function (e.g., ventricular pump function).

This application recognizes that the normal heart has a shape, size and construct that exhibit a relatively uniform configuration with respect to the muscle mass and the blood filled chambers. The ratio of these components remains proportionally similar with changes in heart size. Additionally, the elasticity and compliance of the ventricular muscle has characteristic properties as well. The target profiles (or waveforms) specified here are best suited for the conditions characteristic of such normal hearts. Although the profiles may be suitable to provide relatively good control in diseased hearts, refinements in the profiles may be discovered for specific pathologic conditions and are encompassed within the scope of this application. For example, conditions such as significantly high blood pressure or ventricular outflow obstruction from stiff or stenotic (i.e. narrowed down valve because of diseased condition) valves can lead to a thickened heart muscle. On the other hand, conditions of leaking and/or underperforming valves as well as pathologic shunts that re-circulate blood back into the ventricle can create relatively dilated, thin heart muscles. These two extremes would be expected to alter certain aspects of the target profiles for otherwise normal hearts, and the inventor envisions altering the target profiles to reflect the expected profile or a diseased heart rather than a normal heart.

BRIEF DESCRIPTION OF THE DRAWINGS

The present disclosure will be understood more fully from the detailed description given below and from the accompanying drawings of various implementations of the disclosure. Please note that the dimensions shown in the figures are for illustrative purposes only and not drawn to scale.

FIG. 9 illustrates a table that lists relation between variables used to construct target volume delivery profiles during actuation mode, according to an embodiment of the present disclosure.

FIG. 12 illustrates a table that lists relation between variables used to construct target volume delivery profiles during assist mode, according to an embodiment of the present disclosure.

FIG. 16 illustrates a table that lists relation between variables used to construct target pressure profiles during actuation mode, according to an embodiment of the present disclosure.

FIG. 19 illustrates a table that lists relation between variables used to construct target pressure profiles during assist mode, according to an embodiment of the present disclosure.

FIG. 22 illustrates a table that lists relation between variables used to construct target strain profiles, according to an embodiment of the present disclosure.

FIG. 29 illustrates a table that lists relation between variables used to construct target strain rate profiles, according to an embodiment of the present disclosure.

DETAILED DESCRIPTION

Aspects of the present disclosure are directed to algorithmically controlling effective functioning of a drive system coupled to a device that is configured to provide external mechanical support to an arrested, failing or malfunctioning heart. The device, generically called a pump, can be of any suitable shape to provide external force to the heart from its outside surface. The drive system control is agnostic of the actual shape of the pump or materials used to construct the device. Device control algorithms and determination of pertinent target profiles (e.g., FIGS. 10, 11, 13, 14, 17, 18, 20, 21, 23, 24, 25, 26, 30, 31, 32, 33) for the heart's function are tied to heart sizes. Heart sizes can be estimated/measured with a variety of means and can be expressed either as a linear dimension or as total volume. A non-limiting example of a linear dimension is end-diastolic diameter of the heart at a section (e.g., see the dimension $D_{ED}$ in FIG. 5) along an outer surface. Another non-limiting example of a linear dimension is end-diastolic length of the heart from below atrioventricular valves to the heart's base along a long axis (e.g., see the dimension $L_{ED}$ in FIG. 5). Note that since the pump is coupled to the outer surface of the heart, the heart's dimensions can also be determined from measuring/estimating device dimensions.

Figure 24:
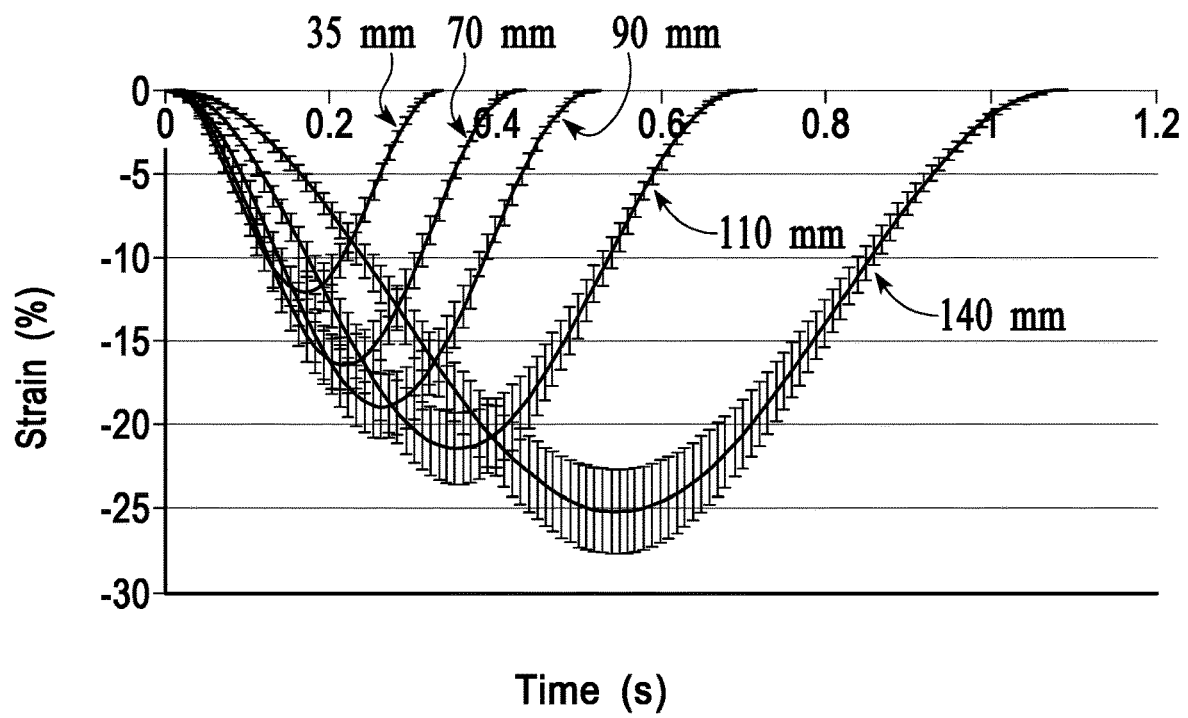
FIG. 24 illustrates target strain profiles for a selected few end-diastolic diameter heart sizes within the 35-140 mm range, represented as (mean±standard deviation), according to an embodiment of the present disclosure.

For either linear dimension or volume, tables (e.g., tables shown in FIGS. 6, 9, 12, 19, 22, and 29) are provided and stored in the memory of a drive system controller to give specified ranges of heart size, and the algorithms predict the target profiles for fluid flow in the drive system (drive volume), device pressure and strain/strain rate in the heart or in a particular heart chamber (e.g., left ventricle (LV) strain). Any of the three target profiles (i.e., fluid flow (drive volume), device pressure, and strain/strain rate) can be used independently to control the device function without the need for hemodynamic feedback. This capability is pivotal in case of an arrested heart, which cannot provide any hemodynamic feedback at least in the beginning when no native contractile function of the arrested heart is available. Note that in the tables in the accompanying figures, the '±' sign indicate fine control setting of varying a quantity (such as the rate 'f' in the tables in FIGS. 9 and 12) rather than a standard deviation around a central value. On the other hand in the graphs, (means±standard deviation) means the curve can move up or down within the standard deviation range shown by the bars, for example as shown in FIG. 24.

The current disclosure provides solutions that allow operation of any pump by measuring only the pressure within the device, flow in its drive system and/or the connections between the drive system and the device. Note that the term "flow" is related to delivery of certain volume of fluid (liquid or gas) to the pump via a drive line coupled to the device. Thus, life-saving support can be reliably provided without being dependent on measures taken from the circulation (i.e. hemodynamic measures). This has many fundamental important implications. Proper regulation of devices which support the heart's function by mechanically actuating heart chambers (e.g., one or more ventricles) remains poorly understood. Although one can change drive controls and drive dynamics while observing the hemodynamic response, the hemodynamic measures can frequently be non-responsive, inadequate or misleading to give any clear indication of how to alter drive system control parameters. Such a circumstance is not unusual in setting of sudden cardiac arrest or cardiovascular collapse, where there is no opportunity to place hemodynamic monitors that might be used for assessing life-saving device intervention. Additionally, even when any hemodynamic information is available, its accuracy and integration with a drive control system can be problematic and the variability in hemodynamic responses can mislead one on how device control can be best adjusted. This patent application describes that, as an alternative to of relying on hemodynamic feedback, controlling the device using measures of flow (volume) and pressure generated by the drive system provides an accurate and reliable means to arrive at proper pump function.

As mentioned in the background section, a heart's pump function can be separated into systolic pump function (i.e., the process of ejecting blood from the heart) and diastolic pump function (the process of filling the heart for the next contraction). These two components are clearly distinct and devices can effect either one or both in fact or in theory. Sometimes acting on just one of the systolic and diastolic component of pump function can lead to a secondary adverse effect on the other. For example, merely compressing the heart with a mechanical device can augment filling. However, absent a concerted and direct beneficial action toward diastolic function, such a device can actually impair diastolic pump function. Therefore the solutions disclosed in this patent application are directed towards the proper independent control of both systolic and/or proper diastolic pump function. This ability is particularly important in conditions of cardiac arrest or very severe heart failure where both the filling (diastolic function) and emptying (systolic function) functions are severely impaired or virtually absent. Irrespective of whether systolic, diastolic, or both systolic/diastolic support is provided, the fundamental common aspect is that mechanical forces, applied external to the heart's surface, are used to aid the weakened or arrested heart in the effective pumping of blood. The conditions where these support mechanisms have relevance would include total circulatory support of an arrested heart, and support of the failing heart that has some degree of native function in which support can benefit and/or augment the heart's systolic or diastolic pump function.

Until this date, the various cardiac support devices' function has predominantly focused on systolic assist. This systolic assist-focused approach has limitations for at least the following reasons: 1) diastolic pump function or the filling of the chambers (e.g., ventricles) is an ailment present in nearly all forms of heart failure and/or cardiac arrest (during cardiac arrest filling is strictly a passive event and most significantly impaired when compared to any degree of heart failure); and 2) devices that merely compress the heart can further compromise diastolic function or heart filling. Therefore, the provision of both systolic and diastolic assist is preferred. The methods disclosed in this patent application pertain to devices that predominantly and/or independently impact either systolic or diastolic or both functions with respect to relevant target profiles.

Figure 1:
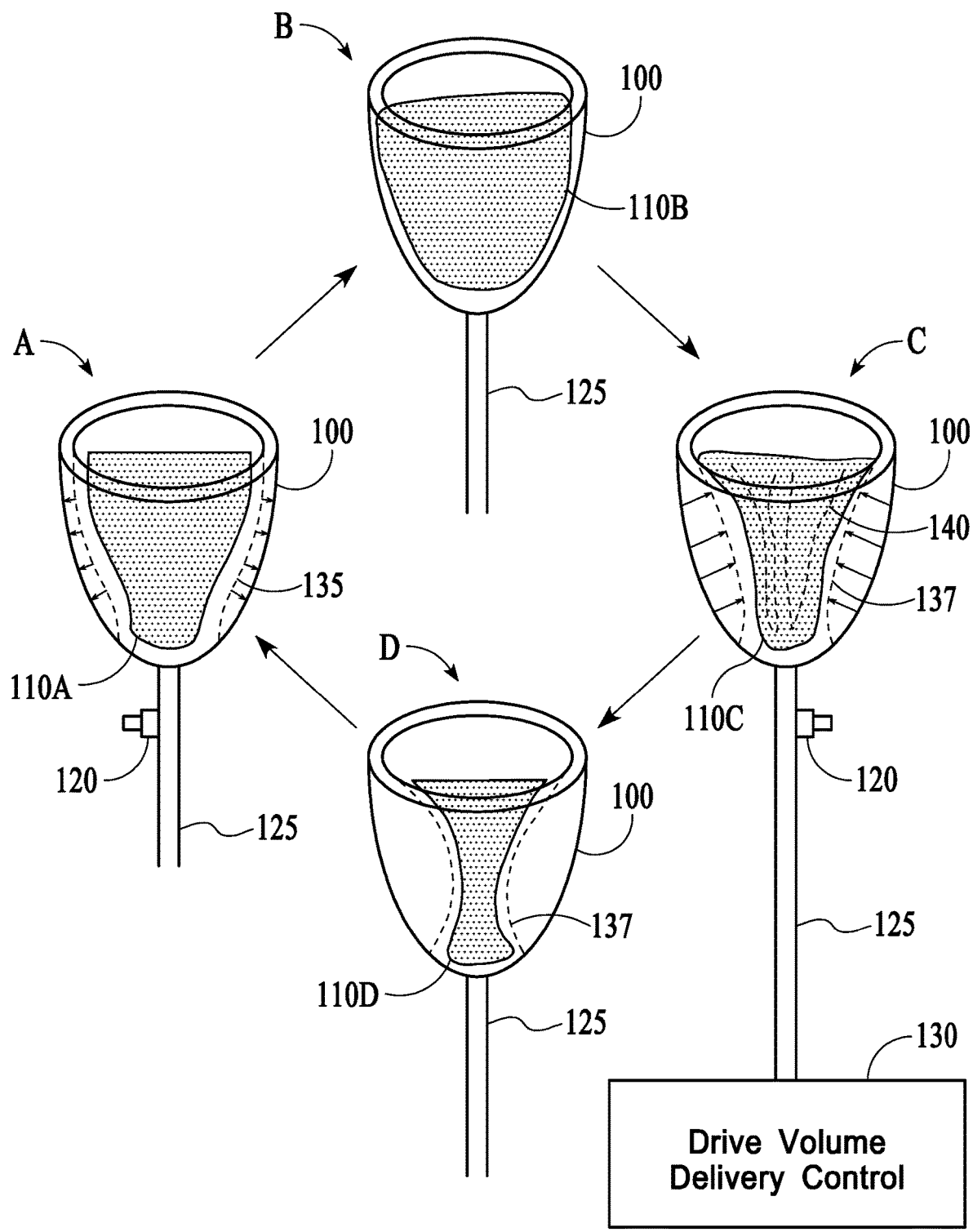
FIG. 1 illustrates a diagram showing the phases of operation of a particular example of a pump, though the shape of the pump can vary from what is shown in FIG. 1. The pump is capable of either or both active systolic and active diastolic support, according to some embodiments of the present disclosure.

FIG. 1 is a schematic that summarizes the phases of cardiac support provided by a mechanical pump 100 that is designed to provide either systolic assist, or diastolic assist or both functions. Note that the figure depicts a mechanical pump 100 that imparts an external force to the ventricles from the outside, but the shape or the device is not important and any portion of the ventricles can be externally acted on as well. The device 100 is connected to drive volume delivery controller 130 via drive line 125. A pressure regulation mechanism 120 may be coupled to the drive line 125 for controlling pressure. Note that the pressure regulation mechanism can be a physical device (e.g., a valve), or the pressure can be regulated simply by controlling the flow of fluid in the drive line 125. Note that both systolic and diastolic assists are indicated, however, as previously stated, not all devices assist diastole. Also note that drive control mechanism can be based on pneumatic or hydraulic depending on the fluid (i.e. liquid or gas) propagating in the drive system. The pump generally operate by control of fluid flow in and out of the devices to regulate systolic and diastolic functions respectively. Additionally, pressure control of such fluid flow within the drive system can generally be accomplished by a valve allowing air to enter or be removed as needed to achieve the target profiles.

Figures 5, 6:
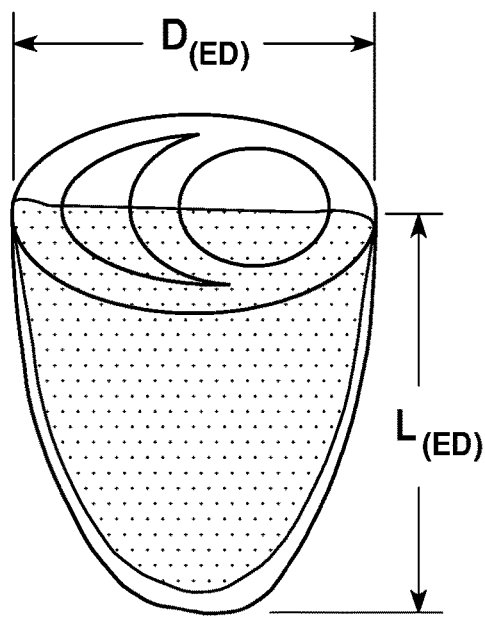
FIG. 5 illustrates a schematic of overall end-diastolic dimension(s) of the heart, such as its short and long axis dimensions, which allow the overall volume of the heart to be estimated/measured when being supported by the device, according to an embodiment of the present disclosure.
FIG. 6 illustrates a table that correlates heart dimension with volume of the heart relevant for the algorithm, according to an embodiment of the present disclosure.

A fundamentally important aspect to the claims in this application is the size of the heart is estimated/measured at any given time. The relevant dimension of the heart depends on its condition prior to device application and the appropriate fit of any given device. However, the estimated/measured size is very accurate when it correlates with the end-diastolic overall size of the heart during device support. Given the heart size can change with device application, the initial estimate/measurement of heart size may change during device support and therefore may need to be re-estimated/re-measured to arrive at the most ideal control profile. The example shown in FIG. 1 illustrates how both the left and right ventricles are acted on by an external force by such pumps. Therefore, the relevant volume of the encompassed portion of the heart would be represented by "volume occupied by the ventricles" at a given time (i.e., 110A during diastolic phase (indicated as "A"), 110B at the end of diastole (indicated as "B"), 110C during the systolic phase (indicated as "C"), and 110D at end of systole (indicated as "D")), and that this volume of the heart itself (and not just the volume of the blood within) is referred to throughout this application. In embodiments of the present application, the volume can be characterized at the time the heart is full at end diastole (110B), defined as the volume occupied by the heart's ventricles and blood within the ventricles at end-diastole ($V_{ED}$), sometimes also called as EDV (end-diastolic volume). Another measure of the heart's size at this point in time is the maximal short-axis of the ventricles at end-diastole or $D_{(ED)}$. This is shown in FIG. 5. The quantities $V_{(ED)}$ and $D_{(ED)}$ are correlated. The volume occupied by ventricles at end-diastole is a principal measure used to calculate the target profiles of fluid flow, device pressure and ventricular strain discussed further in this patent application. Note that volume or diameter can be estimated/measured by a variety of means both before, and during device application. Finally, note that volume can also be estimated/determined at the end of systole ($V_{(Es)}$) (e.g., 110D) or after the blood has been evacuated to whatever extent occurs during compression (or contraction when the heart is beating). The dashed lines 135 in the diastolic phase "A" indicate expansion of heart, while the dashed lines 137 in the systolic phase "C" (and "D") indicate compression/contraction. Dashed lines 140 within the volume 110C in phase "C" indicate systolic strain/strain rate. Though not shown by dash lines, strain/strain rate can be measured within the volume 110A in the diastolic phase "A" as well. The pressure regulation device 120 acts as a diastolic pressure control mechanism in phase "A" and "B", and acts as systolic pressure control mechanism in phases "C" and "D".

Of particular relevance to the claims in this patent application are the independence to hemodynamic measure or any physiologic measure that is typically relied on for the proper control and/or operation of existing pumps. The control algorithms disclosed herein provide means for proper device function based on and estimation/determination of heart size and the volume occupied by the heart. The heart size can simply be estimated/measured based on the patient's body size. The algorithms then repeatedly refer back to heart size which becomes apparent at the time of device application and throughout the support period. Importantly, with respect to this important variable, the device itself serves as a gauge to determine heart size. Furthermore, heart size can actually change throughout support scenarios. For example, when a device is placed on the heart in an emergency (cardiac arrest), the heart may initially be relatively large as it is engorged with blood and dilated. As the heart is pumped, it will eventually assume a smaller more normal size. This leads to appropriate adjustments in the device drive control algorithms to include changing the actual size of the device to conform to the heart.

Another important relevant point to the claims is the typical conditions in which devices may be applied under emergency circumstances. In particular, hemodynamic measures are not readily available. At first, a patient may not even have a blood pressure (e.g., in a cardiac arrest scenario). Once the circulation is regained to a certain capacity by applying external mechanical assistance to the heart, instruments utilized to measure hemodynamic response (e.g., arterial blood pressure catheters placed into the circulatory system, venous lines or more sophisticated devices such as echocardiograph (also referred simply as "echo"))

can require a finite amount of time to install. Therefore, the ability of the controller of the drive system claimed herein to act irrespective of hemodynamic response is of critical importance. It is to be appreciated that, as hemodynamic response measuring devices become available, they can certainly aid to confirm that optimal results are achieved and/or confirm heart size is accurately assessed. All these inputs can be used to assess or refine the pump's functionality, but are not required to match the stored target profiles.

Figure 2:
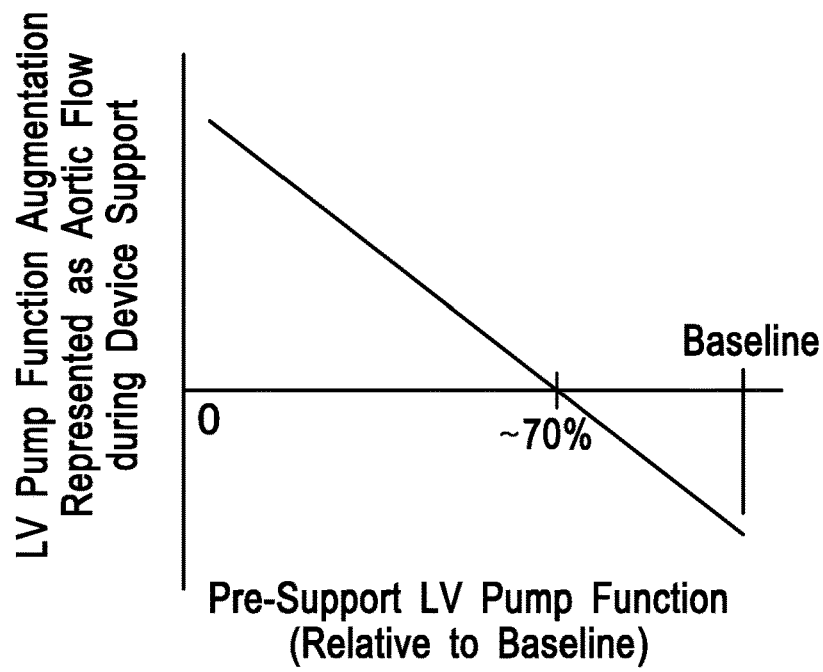
FIG. 2 illustrates augmentation of pump function during device support with varying levels of native cardiac functions, according to an embodiment of the present disclosure.

Current conditions of a heart chamber (such as a ventricle's) function/dysfunction have been identified to guide the control algorithms for the drive system. The most severe degree of heart dysfunction is cardiac arrest where the heart has no native contractile function. In such circumstances, the mode of support is termed "actuation." A set of profiles stored as "actuation" mode profiles (flow profile, pressure profile and/or strain/strain rate profiles) are used in this mode. Lesser degrees of heart failure (i.e. moderate may be treated reasonably with predominant systolic or diastolic assist in which mode of support is termed "assist", and a set of profiles stored as "assist" mode profiles are used. Finally "weaning" is the mode where the heart's natural function is sufficient to sustaining life and the need for external mechanical support is diminished. As shown in FIG. 2, the pump augments the heart's pump function (e.g., pump function of the left ventricle (LV)) the most in the "actuation" mode. The augmentation gradually declines in the "assist" mode, and when the heart's pump function is restored approximately to 70% or other predetermined threshold percentage of the baseline (i.e. the native function level of a normal beating heart), then the augmentation is actually negative, and the pump is "weaned" off. The augmentation is represented by "aortic flow" during device support in FIG. 2. Note that measuring "aortic" flow is just an example of arterial flow.

Figure 3:
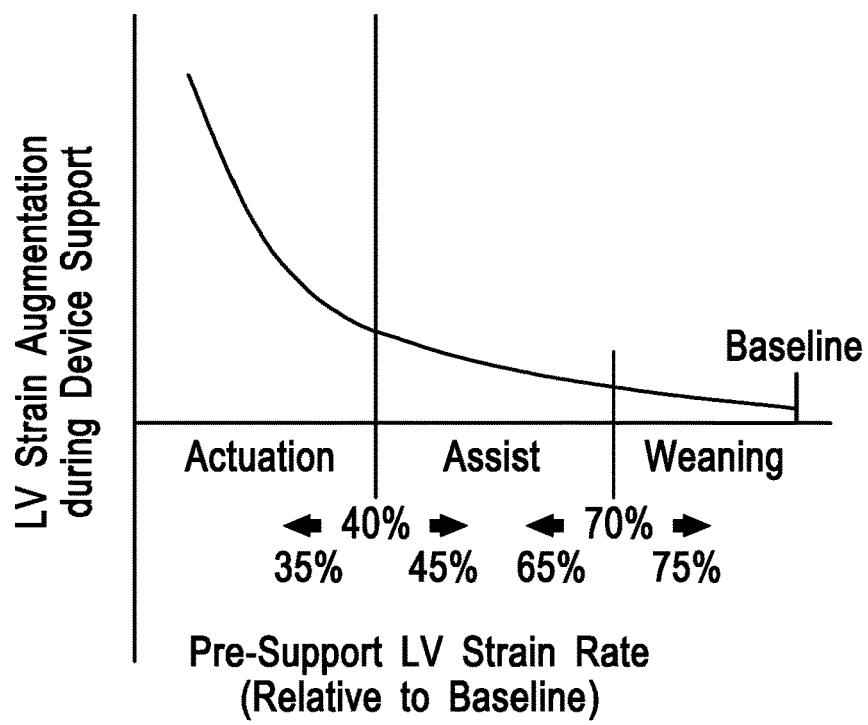
FIG. 3 illustrates augmentation of the heart's contractile function during three modes of device support, i.e. actuation mode, assist mode, and weaning mode, as determined by the presence or absence of native cardiac function, according to an embodiment of the present disclosure.

Another way of visualizing the operational modes of the pump is to map the heart's contractile function during device support relative to the heart's native baseline function. The heart's (or a specific chamber's, e.g., the left ventricle's) contractile function can be represented by strain augmentation with respect to pre-support strain rate, as shown in FIG. 3. In actuation mode, the pre-support LV strain rate relative to baseline is approximately 0-40% or 0-50% or other predefined range. In assist mode, the pre-support LV strain rate relative to baseline is approximately 40-70% or 50-80% or other predefined range. And in the "weaning" mode, the pre-support LV strain rate relative to baseline is approximately 70-100% or 80-100% or other predefined range. Note that these ranges of numbers can be set arbitrarily and they do not limit the scope of the disclosure. For example, weaning from support may be considered at even lower levels of cardiac function. However, the demonstrated benefit of the devices may be limited when cardiac function is at or above 70% baseline. Moreover, "assist" mode profiles may be still applicable during weaning of such devices and may still contribute to cardiac recovery. In this later circumstance, device support may provide little in the way of measurable augmentation of cardiac function, yet substantially aid the heart in recovering its native baseline function.

Figure 4:
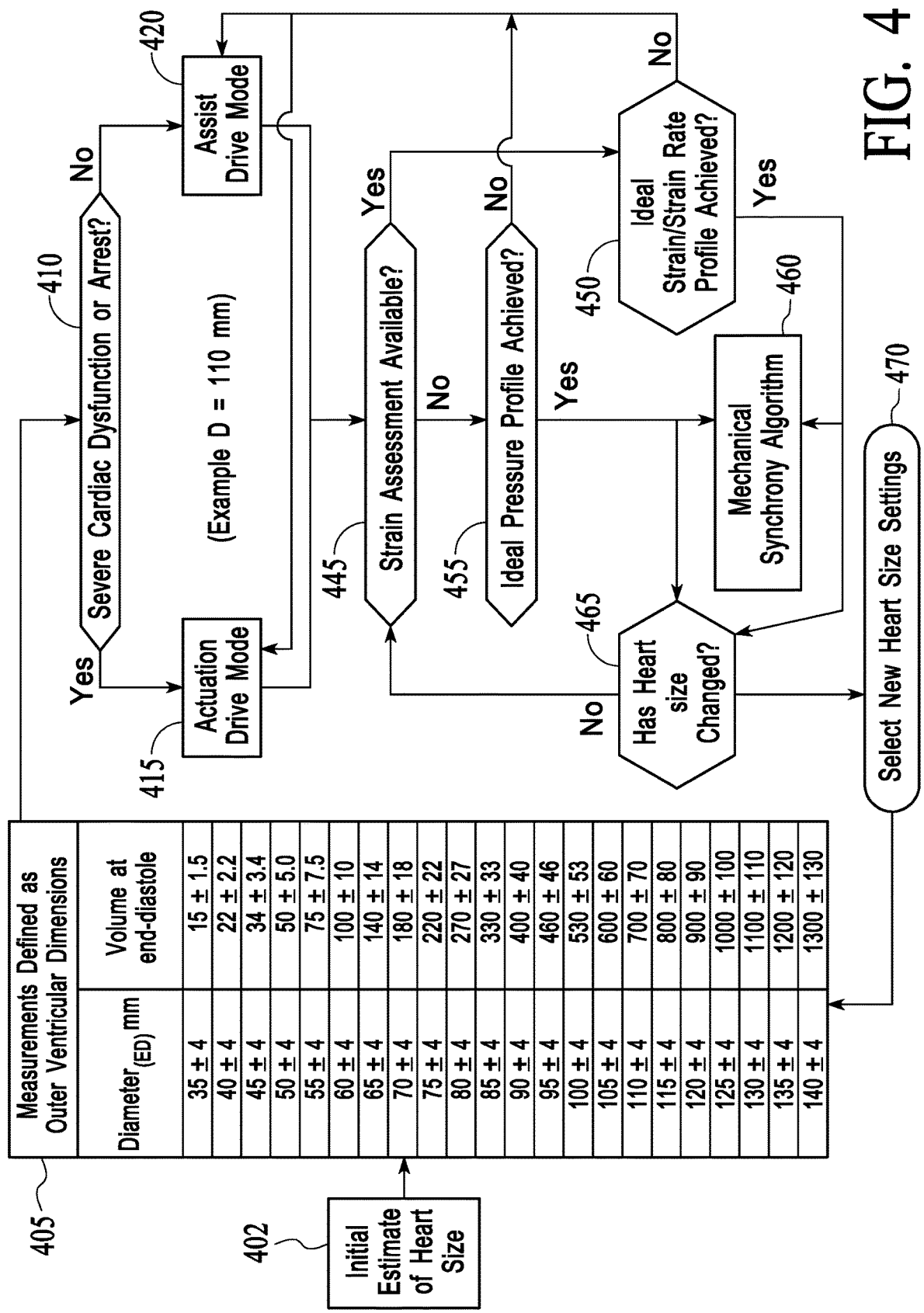
FIG. 4 illustrates a composite flowchart of device control with multiple orders of control, according to an embodiment of the present disclosure.

FIG. 4 shows a composite flowchart for algorithmically controlling a pump, such as device 100 shown in FIG. 1. The algorithms enable providing life-sustaining support using what have been termed "orders" of control. The term "order" has been utilized for clarity for the purposes of explaining the different control algorithms as follows: 1) The first order control refers to the flow of fluid (which can be gas, e.g., air, or a liquid) from the device's drive system to the device. The flow is synonymous to volume displacement within the drive system. This first order of control can be achieved with any variety of pneumatic or hydraulic pumps used to power such a device. The parameters of the fluid flow for delivery to the device are indexed to the estimated/measured heart size (e.g., end-diastolic heart size) and the degree of severity of the heart failure. 2) The second order of control refers to the pressure measured within the device or within the device's drive line (e.g, fluid delivery line, e.g. 125 in FIG. 1) in close proximity to the device or at or within the device. Again, the parameters for pressure-based control are indexed to the heart size and to degree of severity of the heart failure. 3) The third order of control refers to the measure of strain in a heart chamber (e.g., left ventricular strain) which can be acquired by a variety of relevant sensors or gauges within the device or within the vascular system or on the surface of the patient's body. A typical example would be an echocardiogram probe placed at relevant locations. Either strain or strain rate or both can be measured to provide control parameters. The parameters of strain/strain-rate-based control are indexed to heart size. Even though the third order of control may use a physiologic measure, the measure can be achieved in manner that do not require time consuming installation (e.g. an echo probe placed on the surface of the body). Alternatively, the measure can be acquired if integrated within the device itself (e.g., a piezo-electric strain sensor is integrated within the pump to measure change of length of the device.) An additional advantage of the strain/strain-rate based third order control is that the measure of stain can also be applied to the estimation/measurement of heart size as echocardiography can provide updated heart size information relevant to the control algorithms.

As shown in FIG. 4, though each order of control can be independently sufficient to provide an impaired heart's pump function, a top level control algorithm can integrate one or more of these three orders of controls (depending on how many orders of control are available) to further improve pump functionality. In addition, a fourth order of control based on mechanical synchrony of the device with a beating heart (i.e. a heart that has not completely stopped and has some native contractile function remaining) can be used to improve the efficacy of the control algorithm.

Persons skilled in the art would understand that though the profiles for targeted volume flow, pressure, and strain/strain rate curves are provided for both systolic and diastolic ventricular pump function, the scope of this patent application encompasses achieving targeted control of any function of any portion of the heart during its pumping cycle.

Conditions where heart function is measurable (e.g., greater than approximately 20% of normal function), it is possible to synchronize pump's externally provided pump function with the heart's native or intrinsic cyclic pump function. In these circumstances, incorporating the "mechanical synchrony" algorithm becomes beneficial. With greater degrees of underlying native heart function, both "mechanical synchrony" algorithms and "assist" mode profiles become more relevant.

In FIG. 4, 402 indicates that an initial estimate/measurement of heart size is provided to the drive system controller, as each algorithm requires heart size as an input. The heart's size (e.g., end-diastolic diameter) can be estimated/measured either before, during or after the heart is acted on by the device. These estimates/measurements may be made in a variety of manners including, but not limited to, direct measurement during exposure, radiology means (e.g., X-ray) before the pump is applied, echocardiography imaging etc. Also, the device itself can be used to measure heart size based on the device fit. A table, such as the illustrative table 405, is stored in the memory of a processor in the (or coupled to the) drive system controller. The table 405 contains data correlating a dimension of the heart with a corresponding volume of the heart at a specific time. For example, as shown in FIG. 5, the dimension can be DEV at the end of diastole. Volume to be occupied (EDV) at end-diastole could be related to the outer ventricular dimensions. The memory also stores one or more sets of target profiles. For example, one set of target profiles can be target drive volume profiles for fluid flow within the drive system, each target profile of the set corresponding to respective values of the dimension of the heart. Another set of target profiles can be target device pressure profile. Another set of target profiles can be target strain/strain rate profile.

When a dysfunction of the heart is detected at 410, depending on the degree of severity of the dysfunction, an "actuation mode" (415) or an "assist mode" (420) is chosen. Definition of actuation and assist modes are described with respect to FIGS. 2 and 3. Also, a dimension of the heart is estimated/measured, e.g., end-diastolic diameter $D_{ED}$ can be chosen as 110 mm for an average adult human male. For children, the heart size can be smaller, e.g., 70 mm of even smaller.

One or more parameters of fluid flow required within the drive system to match the target drive volume profile is calculated by the processor corresponding to the selected value of the dimension of the heart based on the correlation in the table 405, thereby emulating a first order control of the heart's normal pump function. Note that drive volume control and profiles (i.e., first order control) exist at the level of the drive system. These drive volume target profiles result in functional device control that are derived without the need for hemodynamic measure. Drive volume delivery can be readjusted to match the ideal profile as stored for the particular heart size.

Similarly, one or more parameters of pressure required within or in proximity to the device to match the target pressure profile is calculated by the processor corresponding to the selected value of the dimension of the heart based on the correlation in the table 405, thereby emulating a second order control of the heart's baseline pump function. Pressure profiles can be reassessed to match the ideal pressure profile stored in the memory corresponding to the estimated/measured heart size. Note that both systolic and diastolic pressure profiles are termed profiles for second order control. These profiles can be used to control the device independently of the drive volume profiles and do not require hemodynamic measures. Alternatively, the pressure profiles can be used in addition to the drive volume profiles to refine control of the pump's external mechanical pump function.

A third order of control is based on measurement of strain/strain rate for a particular dimension of the heart, for example, length $L_{ED}$ shown in FIG. 5, which is maximal long-axis dimension once the heart reaches end-diastolic size. In some embodiments, strain control profiles can be derived from the left ventricular (LV) myocardium through imaging such as echocardiography or other methods. The strain/strain rate control profiles can be used to control the device independently and do not require measure of hemodynamics. As shown in FIG. 4, strain/strain rate profiles can be stored in the memory, and can improve the efficacy of the volume-based control (first order) and/or pressure-based control (second order). In other words, if it is determined at 445 that strain assessment is available, then the drive system controller tries to achieve ideal strain/strain rate profile (450) that is stored in the memory.

The heart's size can be re-assessed (465) during device function with numerical fit that achieve near-ideal flow, pressure and strain profiles. It is to be noted that the heart is expected to undergo change in size over time during device applications. Such changes in size would therefore have potential impact on arriving at the target profiles as the target profiles are indexed to heart size. Heart size changes may be relatively sudden as in the initial application of such devices on the arrested, dilated heart that assumes a smaller size in short order. On the other hand, such changes can occur more gradually over time as the heart may "reverse re-model" to a more normal shape during its recovery from a diseased/impaired state. The later type of geometric changes in heart size can take from days to weeks or even months depending on the potential reversibility of the heart's underlying ailment and/or the opportunity to address mitigating factors (e.g., valve replacement, coronary stenting etc.). The table 405 can be updated with new heart size information available at 470.

The fourth order of device control relates to the beating heart. In other words, this order of control, referred to as "mechanical synchrony" (460) only pertains to hearts which has some contractile function. In other words, a heart in arrest or without any significant contractile function cannot utilize the mechanical synchrony algorithm. This fourth order of control does not require any input with relation to heart size but does require some type of input with regards to the systolic function of the heart. Specifically, an input that provides a peak of the heart's developed pressure (455) (e.g., peak arterial or systolic pressure or peak heart chamber pressure, such as left ventricle systolic pressure) or the peak in blood flow or the peak in strain rate. This input is utilized in comparison to the device's peak systolic drive pressure to follow the described algorithm. Again as with the three prior orders of control, this fourth order of control can either be utilized independently or integrated with the other orders to improve device control.

The mechanical synchrony algorithm is an independent means for synchronizing device function to heart function. Mechanical synchrony can be accomplished without hemodynamic measures when device actuation is synchronized with strain. Alternatively, measure of physiologic pulsations within the heart chamber (e.g., left ventricle) or arterial circulation can be used, or electrocardiograms when available (see FIGS. 34 and 35 and the related discussion below).

FIG. 6 shows an example table (Table 1) which correlates ventricular mass (volume) at end-diastole based on short-axis diameter $D_{ED}$, as shown in FIG. 5. Note that other relevant dimension of the heart can be used too. For example $L_{ED}$, the length along the long-axis, as shown in FIG. 5, can also be a dimension indicative of heart size for some tables. This type of table can be stored in the controller's memory, as shown in FIG. 4.

FIGS. 7-14 pertain to the flow-based (or volume-based) algorithmic control of the pump (first order control).

Figure 7:
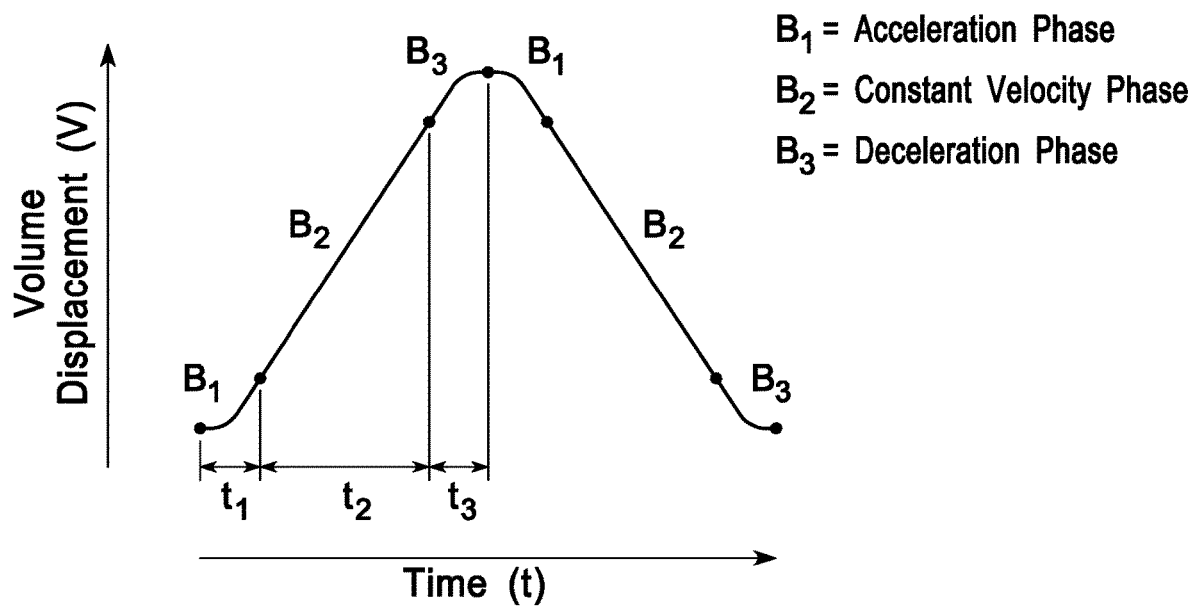
FIG. 7 illustrates an example drive volume displacement profile with constant velocity phase, according to an embodiment of the present disclosure.

Specifically, FIG. 7 is a graphic depiction of control of flow (i.e. the first order control) using a constant velocity. This figure describes how the drive system flow can be targeted graphically and depicts general areas of constant velocity positive drive flow control on the left side of the peak (that leads to cardiac compression or systolic actuation by the device) and constant velocity negative drive flow control on the right side of the peak (this leads to cardiac expansion or diastolic actuation by the device). Note that these target profiles can be separated into systolic and diastolic control profiles, and the device can provide either systolic or diastolic actuation independently.

A volume displacement caused by the fluid flow during the acceleration phase (B1, for time period t1) is governed by the equation:

$$V(t) = (0.5at^2)A_c, \quad \text{(Eq. 1)}$$

where V(t) is volume displacement waveform, t is time, a is acceleration, and $A_c$ is area of a cross section where fluid flow is measured. A volume displacement caused by the fluid flow during the deceleration phase (B3, for time period t3) is governed by the equation:

$$V(t) = (v_{max} - 0.5at^2)A_c, \quad \text{(Eq. 2)}$$

where V(t) is volume displacement waveform, t is time, a is acceleration, Ac is area of the cross section where fluid flow is measured, and $v_{max}$ is a maximum velocity. Each of the positive flow portion and the negative flow portion also comprises a constant velocity phase, and a volume displacement caused by the fluid flow during the constant velocity phase (B2, for the time period t2) is governed by the equation:

$$V(t) = (v_{max}t)A_c \quad \text{(Eq. 3)}$$

where V(t) is volume displacement waveform, t is time, $A_c$ is area of the cross section where fluid flow is measured, and $v_{max}$ is a maximum velocity which is constant in the constant velocity phase.

Figure 8:
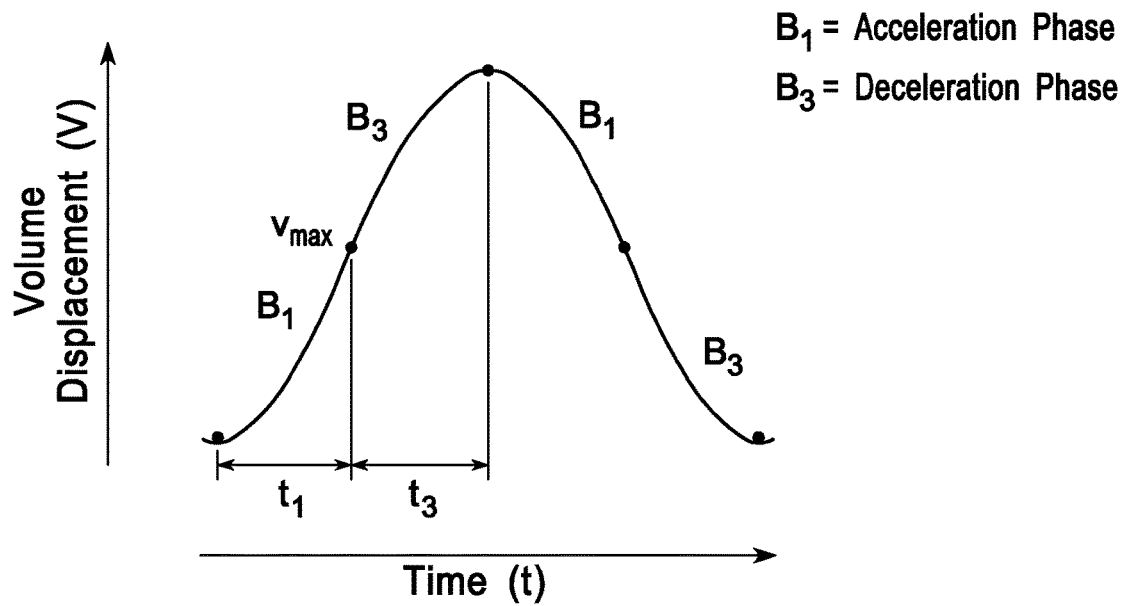
FIG. 8 illustrates an example drive volume displacement profile without constant velocity phase, according to an embodiment of the present disclosure.

FIG. 8 is a graphic depiction of control of flow (i.e. the first order control) without a constant velocity phase. The formula used to generate the non-constant flow curve are the same as Equations 1 and 2 respectively for the phases B1 and B3 shown in FIG. 8. Note that the volume changes are not constrained by specific chamber dimensions. Positive flow is on the left side of the peak and negative flow is on the right side of the peak.

FIG. 9 shows a table (Table 2) that lists the variables used to construct target volume delivery waveforms during actuation mode without a constant velocity phase. The actuation rate 'f' and the linear displacement 'x' within the drive line related to the variables of Equations 1-3 are as follows (where t is time):

$$V(t) = xA_c; \quad \text{(Eq. 4a)}$$

$$a = f^2\left(\frac{x}{225}\right); \quad \text{(Eq. 4b)}$$

$$v_{max} = \sqrt{ax}; \quad \text{(Eq. 4c)}$$

Figure 10:
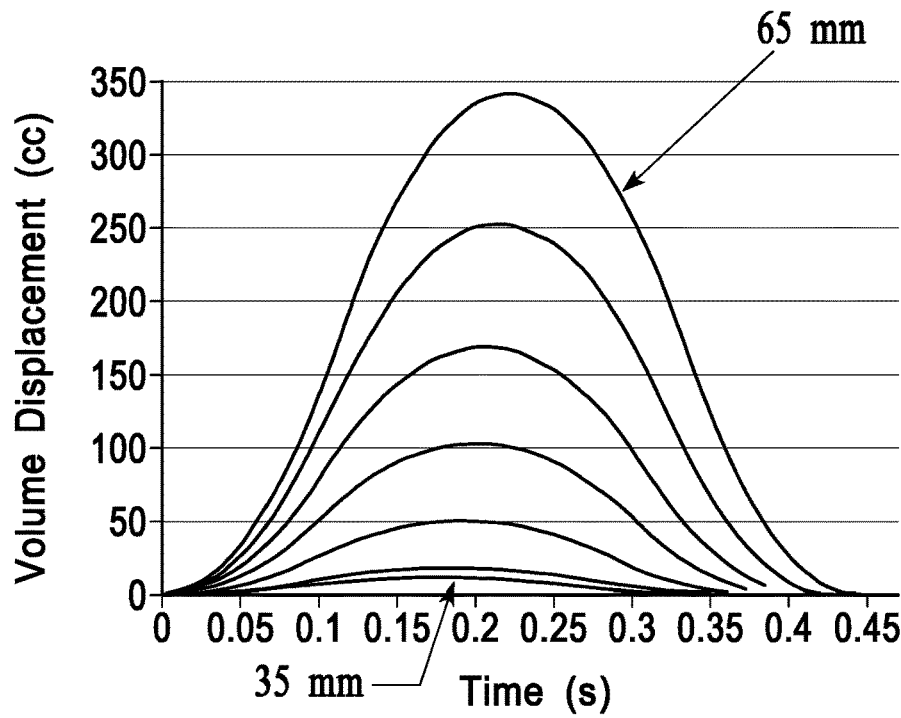
FIG. 10 illustrates target drive volume delivery profiles during actuation mode for 35-65 mm end-diastolic diameter heart sizes, according to an embodiment of the present disclosure.
Figure 11:
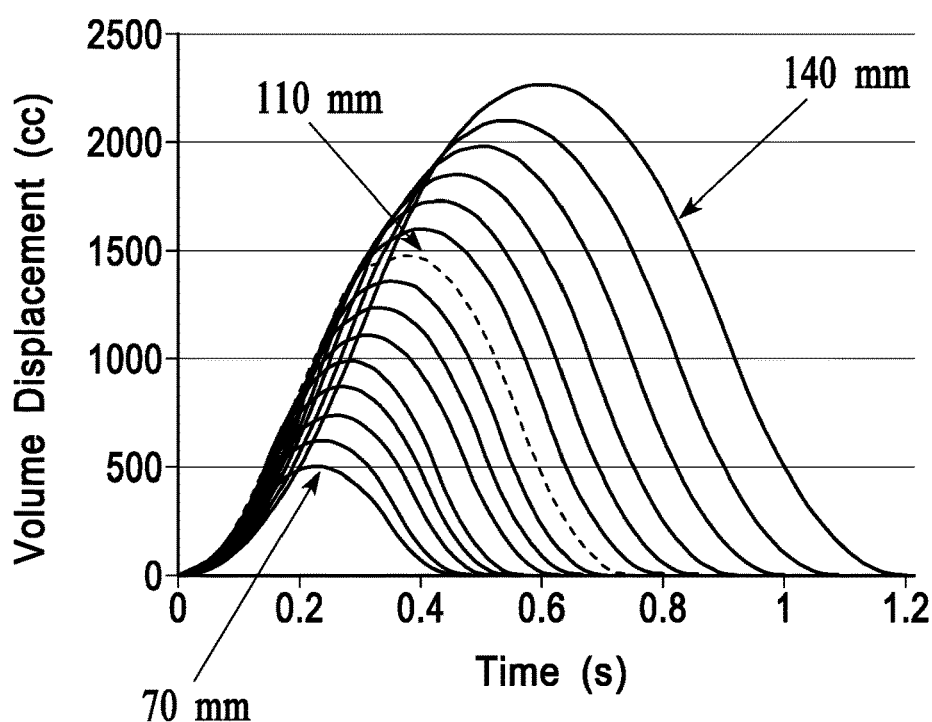
FIG. 11 illustrates target drive volume delivery profiles during actuation mode for 70-140 mm end-diastolic diameter heart sizes, according to an embodiment of the present disclosure.

FIG. 10 illustrates target drive volume delivery profiles during actuation mode (for severely failing heart) for 35-65 mm end-diastolic diameter heart sizes (curves shown for 5 mm increment of diameter, though all the curves are not individually labeled), according to an embodiment of the present disclosure. FIG. 11 illustrates target drive volume delivery profiles during actuation mode (for severely failing heart) for 70-140 mm end-diastolic diameter heart sizes (curves shown for 5 mm increment of diameter), according to an embodiment of the present disclosure. Again, note that the systolic and diastolic drive flow delivery profiles can be used independently to target control of compression and dilation respectively. The profiles of FIGS. 10 and 11 are generated using equations 4a-c (based on equations 1-2) and Table 2 in FIG. 9, where the linear displacement 'x' is calculated based on volume displacement for device-specific pump.

FIG. 12 illustrates a table (Table 3) that lists relation between variables used to construct target volume delivery profiles during assist mode, without a constant velocity phase.

Figure 13:
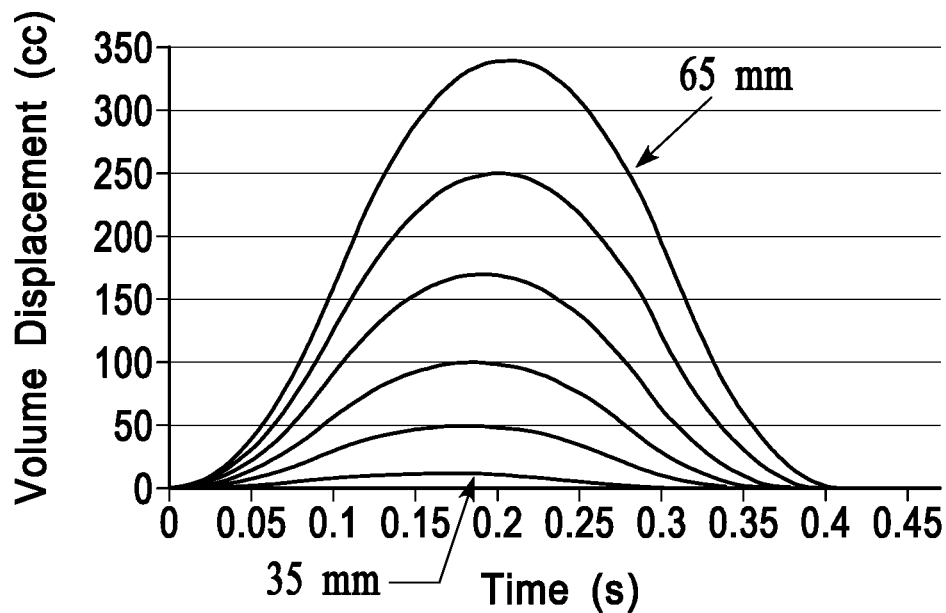
FIG. 13 illustrates target drive volume delivery profiles during assist mode for 35-65 mm end-diastolic diameter heart sizes, according to an embodiment of the present disclosure.
Figure 14:
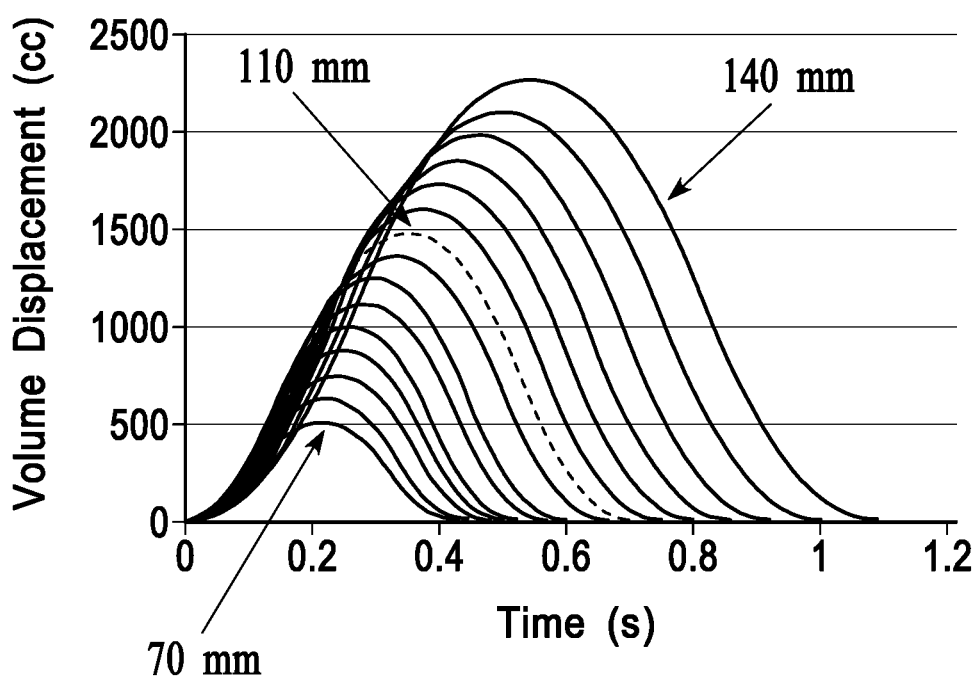
FIG. 14 illustrates target drive volume delivery profiles during assist mode for 70-140 mm end-diastolic diameter heart sizes, according to an embodiment of the present disclosure.

FIG. 13 illustrates target drive volume delivery profiles during assist mode for 35-65 mm (curves shown for 5 mm increment of diameter) end-diastolic diameter heart sizes, according to an embodiment of the present disclosure. FIG. 14 illustrates target drive volume delivery profiles during assist mode for 70-140 mm end-diastolic diameter heart sizes (curves shown for 5 mm increment of diameter), according to an embodiment of the present disclosure. As discussed before, assist mode is to support a failing heart which may have regained some of its native contractile function. The profiles of FIGS. 13 and 14 are generated using equations 4a-c (based on equations 1-2) and Table 3 in FIG. 12. Systolic and diastolic drive flow delivery profiles can be used independently to target control of compression and dilation respectively.

FIGS. 15-21 pertain to the pressure-based algorithmic control of the pump (second order control).

Figure 15:
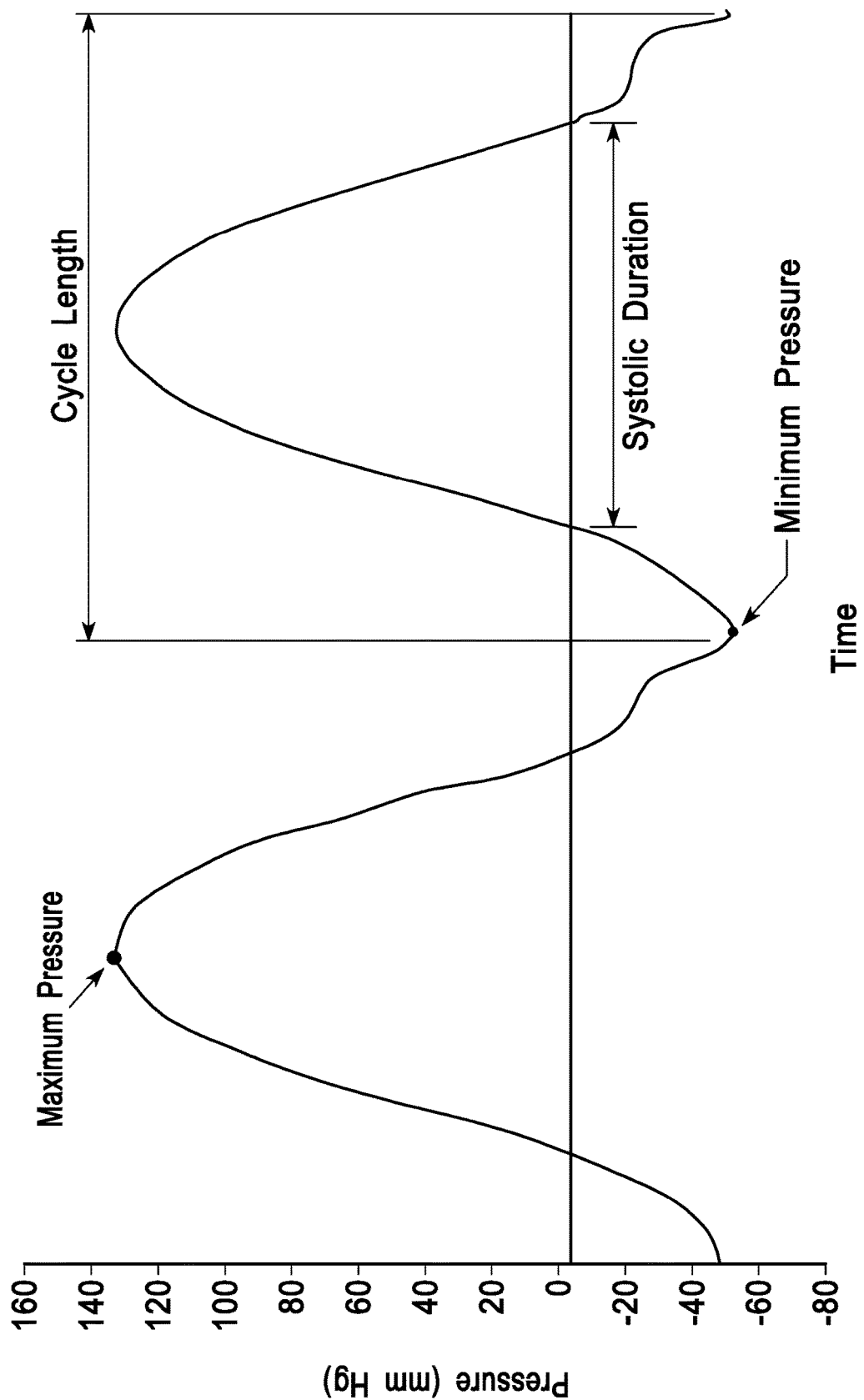
FIG. 15 illustrates a schematic example of how a device pressure profile can be defined, according to an embodiment of the present disclosure.

Specifically, FIG. 15 illustrates target pressure profiles (for second order control) at, near or within the pump. These profiles can be separated into systolic and diastolic device control profiles. The formula used to derive the pressure profile is as follows:

$$P(t) = \frac{(|A_{max}| + |A_{min}|)}{2}[\sin(2\pi ft - \pi/2)] + \left[\frac{(|A_{max}| + |A_{min}|)}{2} - |A_{min}|\right] \quad \text{(Eq. 5)}$$

where P(t) is target device pressure profile, $A_{max}$ is peak amplitude for positive device pressure, $A_{min}$ is peak amplitude for negative device pressure, t is time, and f is actuation rate. Note that $A_{max}$, $A_{min}$, and f correspond to a heart size at a specific time in the heart's cyclic pump function, e.g. at end-diastole.

FIG. 16 illustrates a table (Table 4) that lists relation between the variables used in Equation 5 for ideal device pressure profile in the actuation mode.

Figure 17:
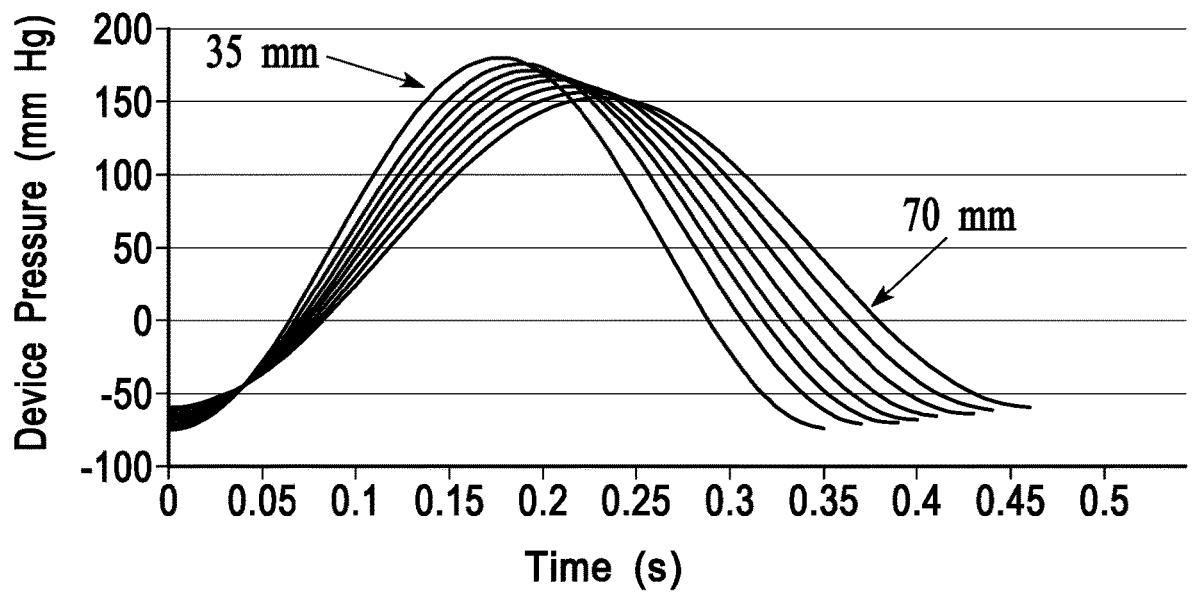
FIG. 17 illustrates target pressure profiles during actuation mode for 35-65 mm end-diastolic diameter heart sizes, according to an embodiment of the present disclosure.
Figure 18:
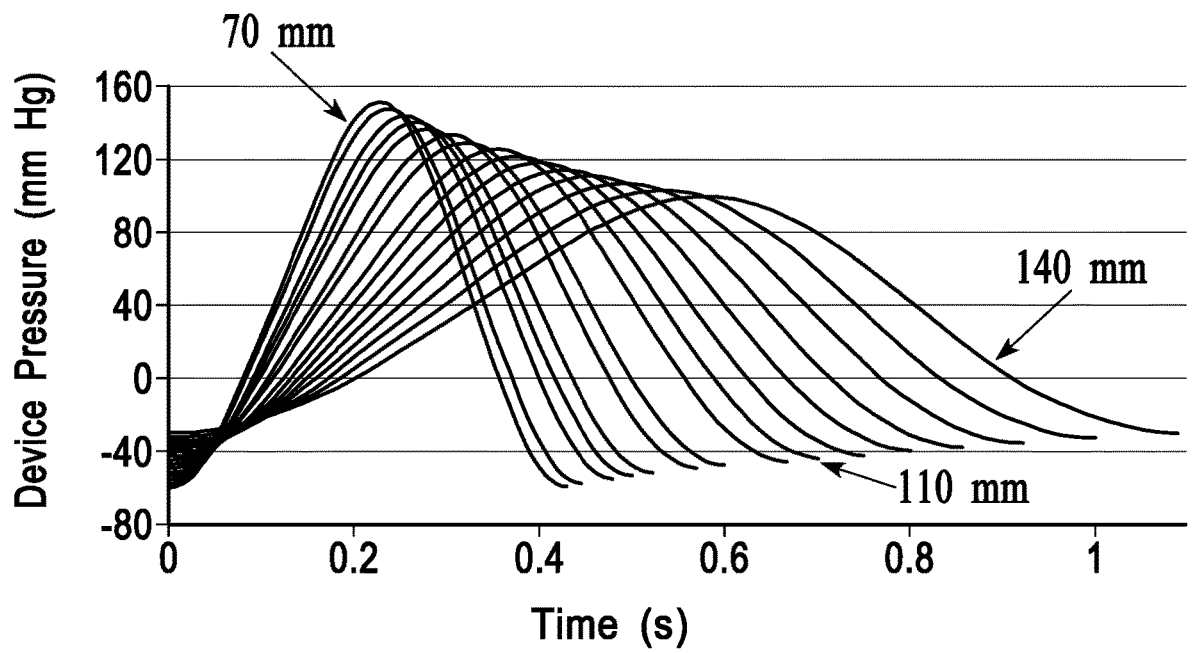
FIG. 18 illustrates target pressure profiles during actuation mode for 70-140 mm end-diastolic diameter heart sizes, according to an embodiment of the present disclosure.

FIG. 17 illustrates target pressure profiles during actuation mode for 35-65 mm end-diastolic diameter heart sizes (curves shown for 5 mm increment of diameter). FIG. 18 illustrates target pressure profiles during actuation mode for 70-140 mm end-diastolic diameter heart sizes(curves shown for 5 mm increment of diameter), according to an embodiment of the present disclosure. Actuation mode is for severely failing heart. Systolic and diastolic control profiles can be generated and matched independently.

Figure 20:
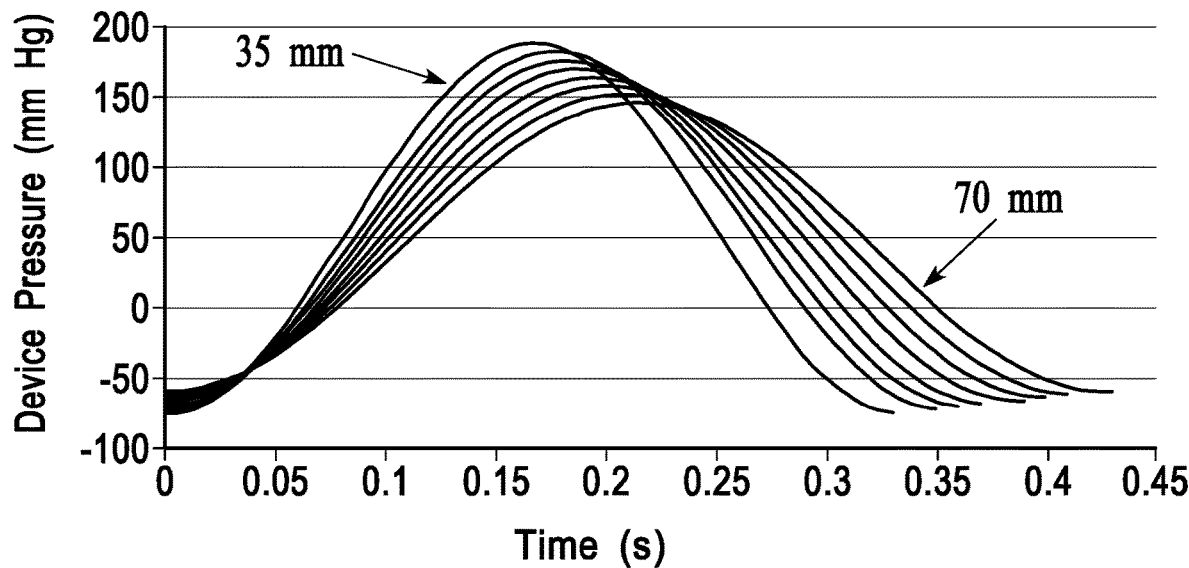
FIG. 20 illustrates target pressure profiles during assist mode for 35-65 mm end-diastolic diameter heart sizes, according to an embodiment of the present disclosure.
Figure 21:
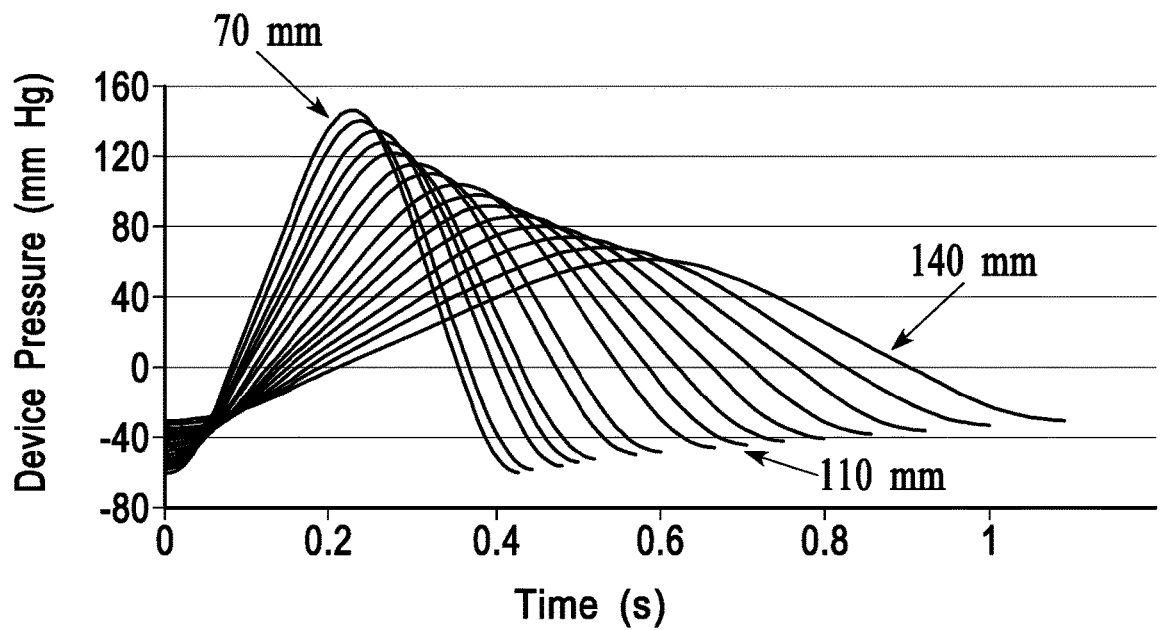
FIG. 21 illustrates target pressure profiles during assist mode for 70-140 mm end-diastolic diameter heart sizes, according to an embodiment of the present disclosure.

FIG. 19 illustrates a table (Table 5) that lists relation between variables used in Equation 5 to construct target pressure profiles during assist mode. FIG. 20 illustrates target pressure profiles during assist mode for 35-65 mm end-diastolic diameter heart sizes (curves shown for 5 mm increment of diameter), according to an embodiment of the present disclosure. FIG. 21 illustrates target pressure profiles during assist mode for 70-140 mm end-diastolic diameter heart sizes (curves shown for 5 mm increment of diameter), according to an embodiment of the present disclosure. Systolic and diastolic control profiles can be generated and matched independently.

Note that the actual pressure profiles can be generated using trend line/numerical best fit to higher order polynomials.

FIGS. 22-33 pertain to the strain-based (or strain rate-based) algorithmic control of the pump (third order control). Note that in case of an arrested heart, where the heart's native pump function is almost non-existent, strain/strain rate can be used to create a pump function. Alternatively, strain/strain rate can be used to augment heart's pump function in a situation where the heart retains certain degree of its native pump function. Strain/strain rate can be an independent means of controlling the heart's pump function, or can work in conjunction with other orders of control, e.g., flow-based control and/or pressure-based control.

FIG. 22 illustrates a table (Table 6) used listing the variables to calculate target strain profiles (for third order control) measured across the patient's body with probes or from the circulatory system. The formula used to derive the instantaneous strain profile is as follows:

$$\varepsilon(t) = \frac{(|\varepsilon_{max}|)}{2} \left[ \left[ \sin\left(2\pi f t - \frac{3\pi}{2}\right) - 1 \right] \right] \quad \text{(Eq. 6)}$$

where ε(t) is target longitudinal strain profile for a portion of the heart (e.g., left ventricle), $\varepsilon_{max}$ is maximum strain for given heart diameter (e.g., $D_{ED}$), t is time, and f is actuation rate.

Note that the strain can also be calculated as a percentage relative to baseline using the formula below:

$$\% \, \varepsilon(t) = 100 \left[ \left[ \sin\left(2\pi f t - \frac{3\pi}{2}\right) - 1 \right] \right] \quad \text{(Eq. 7)}$$

where % ε(t) is target longitudinal strain profile as a percentage relative to baseline for a portion of the heart (e.g., left ventricle), t is time, and f is actuation rate.

Figure 23:
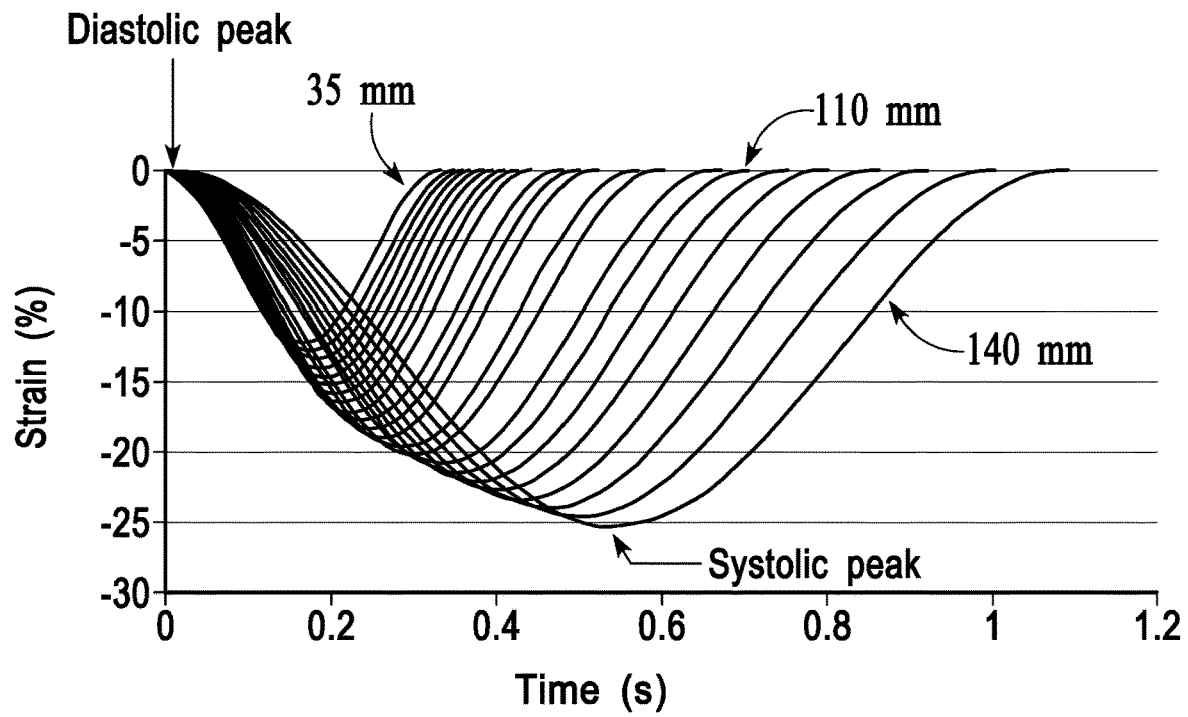
FIG. 23 illustrates target strain profiles for 35-140 mm end-diastolic diameter heart sizes, according to an embodiment of the present disclosure.
Figure 25:
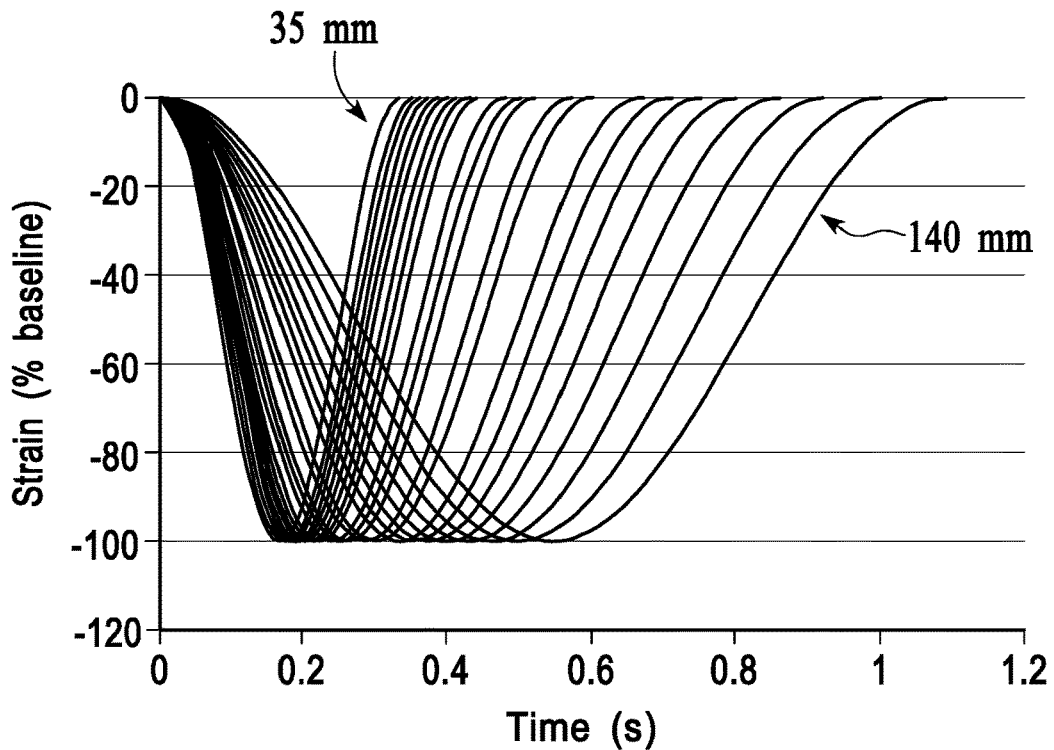
FIG. 25 illustrates target strain profiles for 35-140 mm end-diastolic diameter heart sizes, plotted relative to estimates/measurement of baseline physiology, according to an embodiment of the present disclosure.
Figure 26:
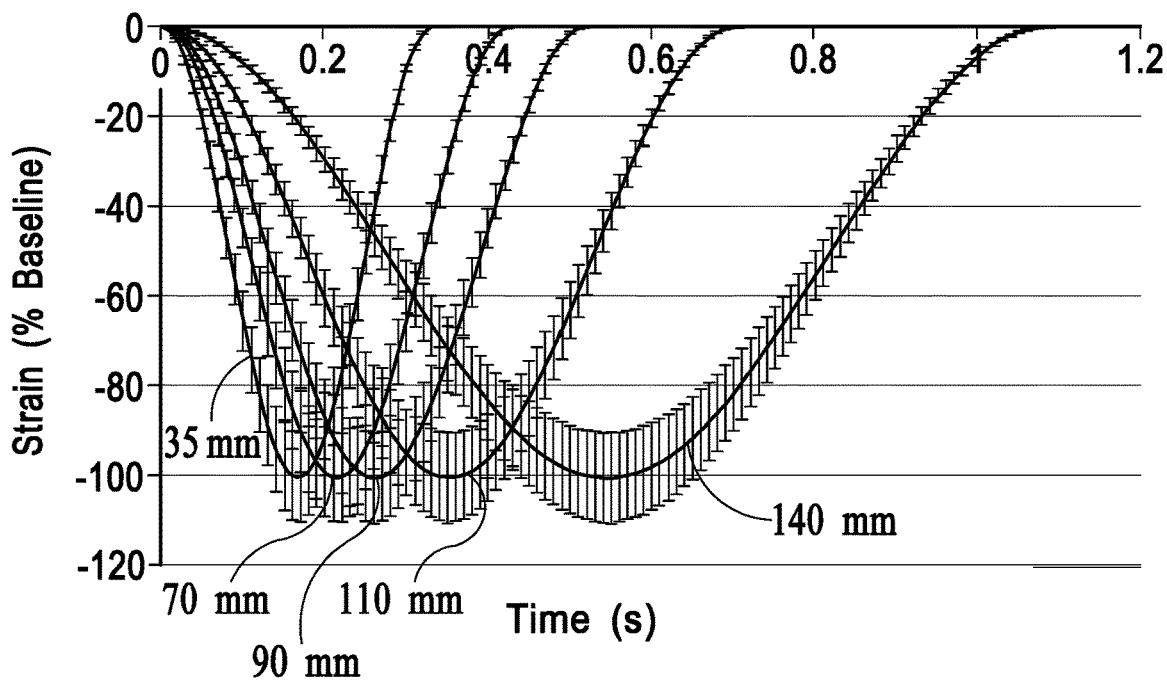
FIG. 26 illustrates target strain profiles for a selected few end-diastolic diameter heart sizes within the 35-140 mm range, represented as (mean±standard deviation), and plotted relative to estimates/measurements of baseline physiology, according to an embodiment of the present disclosure.

FIG. 23 illustrates target strain profiles for 35-140 mm (curves shown for 5 mm increment of diameter) end-diastolic diameter heart sizes, using equation 6. FIG. 24 illustrates target strain profiles for a selected few end-diastolic diameter heart sizes within the 35-140 mm range, represented as (mean±standard deviation). FIG. 25 illustrates target strain profiles for 35-140 mm end-diastolic diameter heart sizes (curves shown for 5 mm increment of diameter), plotted relative to baseline physiology (using Equation 7). FIG. 26 illustrates target strain profiles for a selected few end-diastolic diameter heart sizes within the 35-140 mm range, represented as (mean±standard deviation), and plotted relative to baseline physiology.

Figure 27:
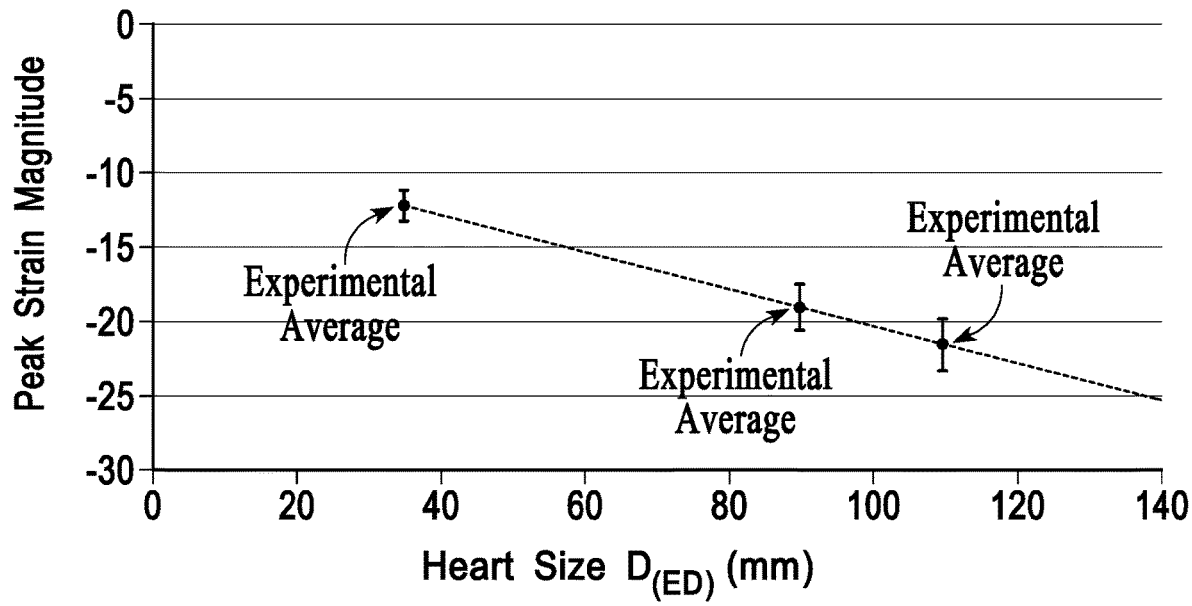
FIG. 27 illustrates a graph of experimental average of peak strain magnitude plotted against varying heart size, according to an embodiment of the present disclosure.
Figure 28:
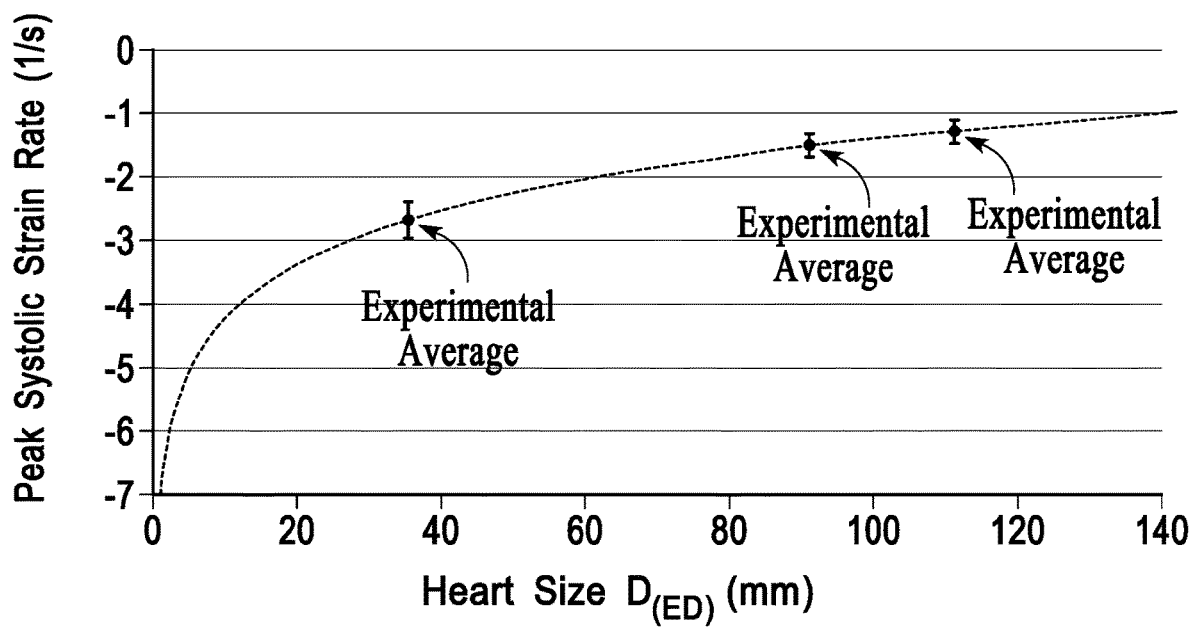
FIG. 28 illustrates a graph of experimental average of peak systolic strain rate magnitude plotted against varying heart size, according to an embodiment of the present disclosure.

FIG. 27 illustrates a graph of experimental average of peak strain magnitude plotted against varying heart size using a numerical fit equation, according to an embodiment of the present disclosure. FIG. 28 illustrates a graph of experimental average of peak systolic strain rate magnitude plotted against varying heart size (using a numerical fit equation), according to an embodiment of the present disclosure.

FIG. 29 illustrates a table (Table 7) used listing the variables to calculate target strain rate profiles (for an alternative to strain-based third order control) measured across the patient's body with probes or from the circulatory system. The formula used to derive the instantaneous strain profile is as follows:

$$\varepsilon'(t) = \varepsilon'_{max} \left[ \sin(2\pi f t - \frac{\pi}{2}) \right] \quad \text{(Eq. 8)}$$

where ε'(t) is target longitudinal strain rate profile for a portion of the heart (e.g., left ventricle), $\varepsilon'_{max}$ is maximum strain rate for given heart diameter (e.g., $D_{ED}$), t is time, and f is actuation rate.

Figure 30:
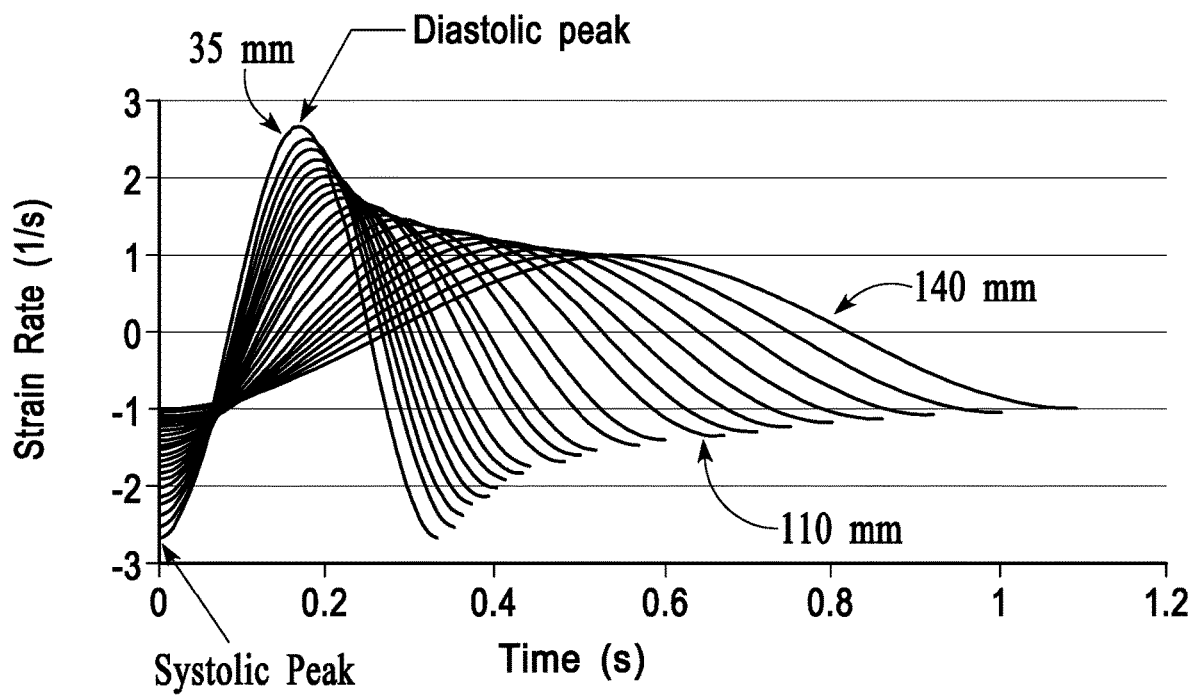
FIG. 30 illustrates target strain rate profiles for 35-140 mm end-diastolic diameter heart sizes, according to an embodiment of the present disclosure.
Figure 31:
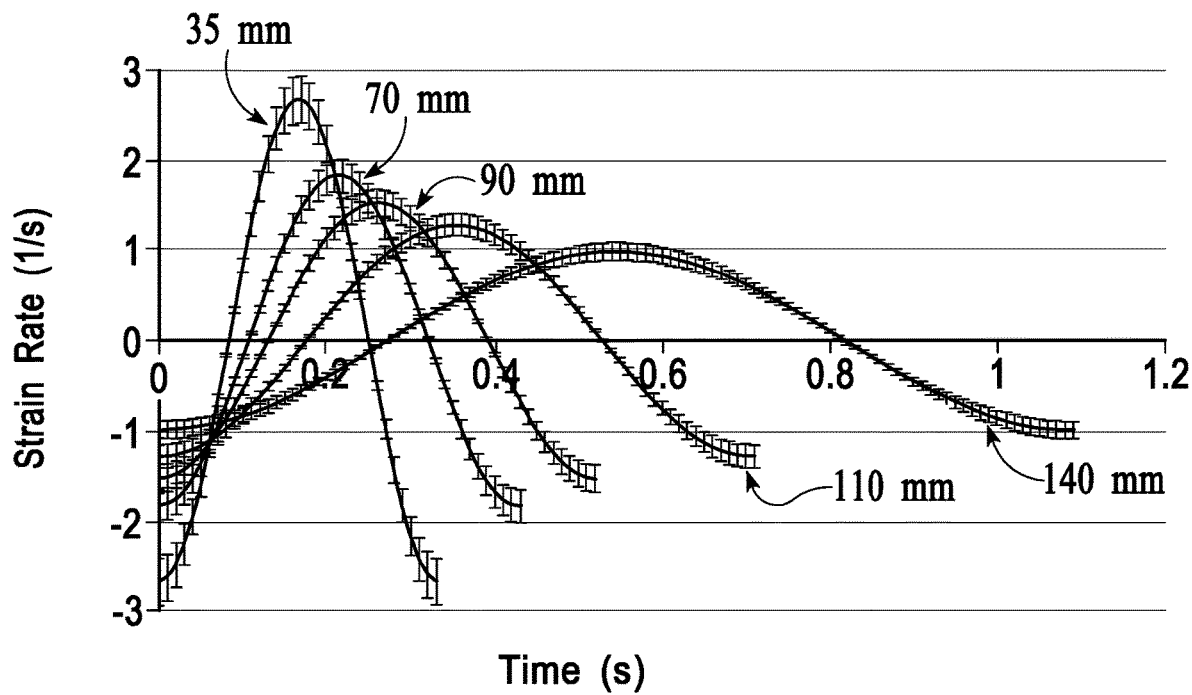
FIG. 31 illustrates target strain rate profiles for a selected few end-diastolic diameter heart sizes within the 35-140 mm range, represented as (mean±standard deviation), according to an embodiment of the present disclosure.

FIG. 30 illustrates target strain rate profiles for 35-140 mm end-diastolic diameter heart sizes. FIG. 31 illustrates target strain rate profiles for a selected few end-diastolic diameter heart sizes within the 35-140 mm range, represented as (mean±standard deviation).

Note that the strain rate can also be calculated as a percentage relative to baseline using the formula below:

$$\% \, \varepsilon'(t) = 100 \left[ \sin(2\pi f t - \frac{\pi}{2}) \right] \quad \text{(Eq. 9)}$$

where % ε'(t) is target longitudinal strain rate profile as a percentage relative to baseline for a portion of the heart (e.g., left ventricle), t is time, and f is actuation rate.

Figure 32:
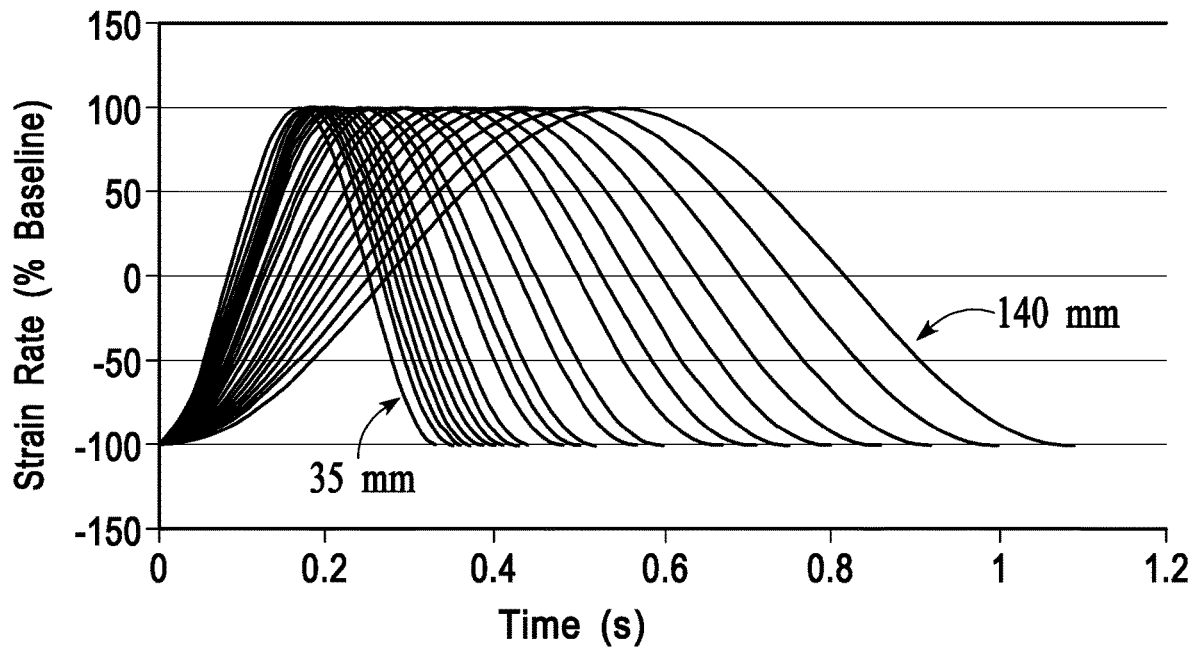
FIG. 32 illustrates target strain rate profiles for 35-140 mm end-diastolic diameter heart sizes, plotted relative to estimates/measurements of baseline physiology, according to an embodiment of the present disclosure.
Figure 33:
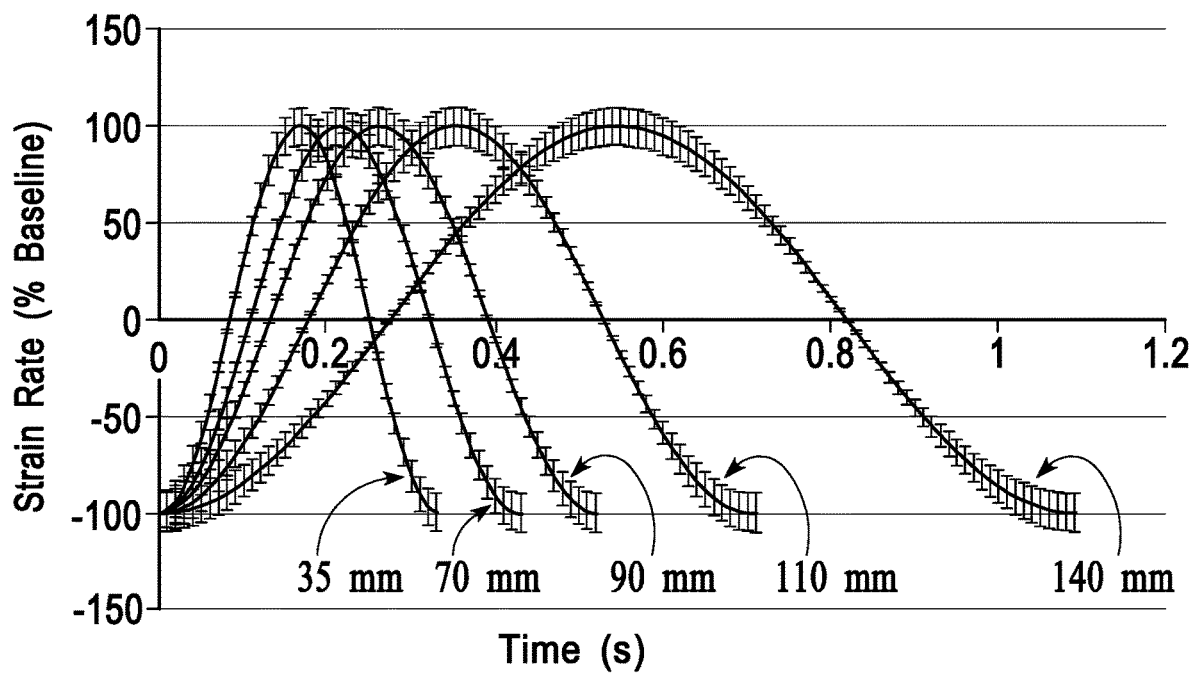
FIG. 33 illustrates target strain rate profiles for a selected few end-diastolic diameter heart sizes within the 35-140 mm range, represented as (mean±standard deviation), and plotted relative to baseline physiology, according to an embodiment of the present disclosure.

FIG. 32 illustrates target strain rate profiles for 35-140 mm end-diastolic diameter heart sizes (curves shown for 5 mm increment of diameter), plotted relative to baseline physiology. FIG. 33 illustrates target strain rate profiles for a selected few end-diastolic diameter heart sizes within the 35-140 mm range, represented as (mean±standard deviation), and plotted relative to baseline physiology.

Figure 34:
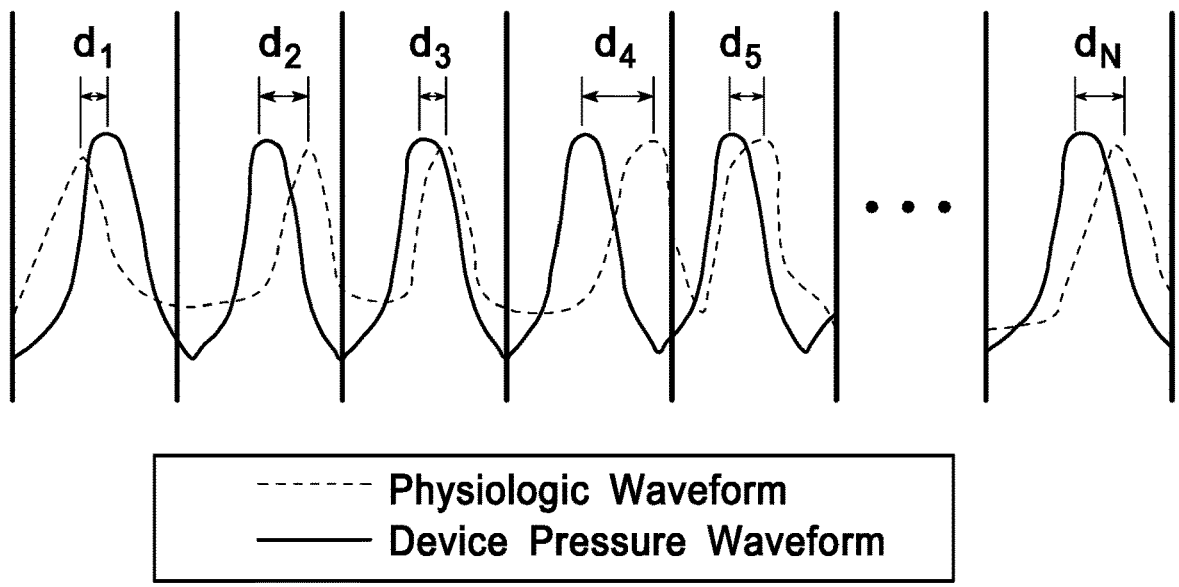
FIG. 34 illustrates a scheme for detecting higher variability between device pressure and the physiologic waveform from a beating heart, as compared for the mechanical synchrony algorithm, according to an embodiment of the present disclosure.
Figure 35:
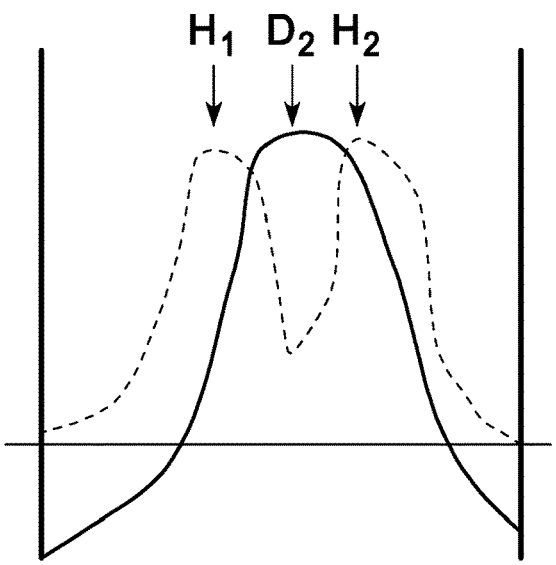
FIG. 35 illustrates identification of the cycles featuring loss of ventricular capture, as part the mechanical synchrony algorithm, according to an embodiment of the present disclosure.
Figure 36:
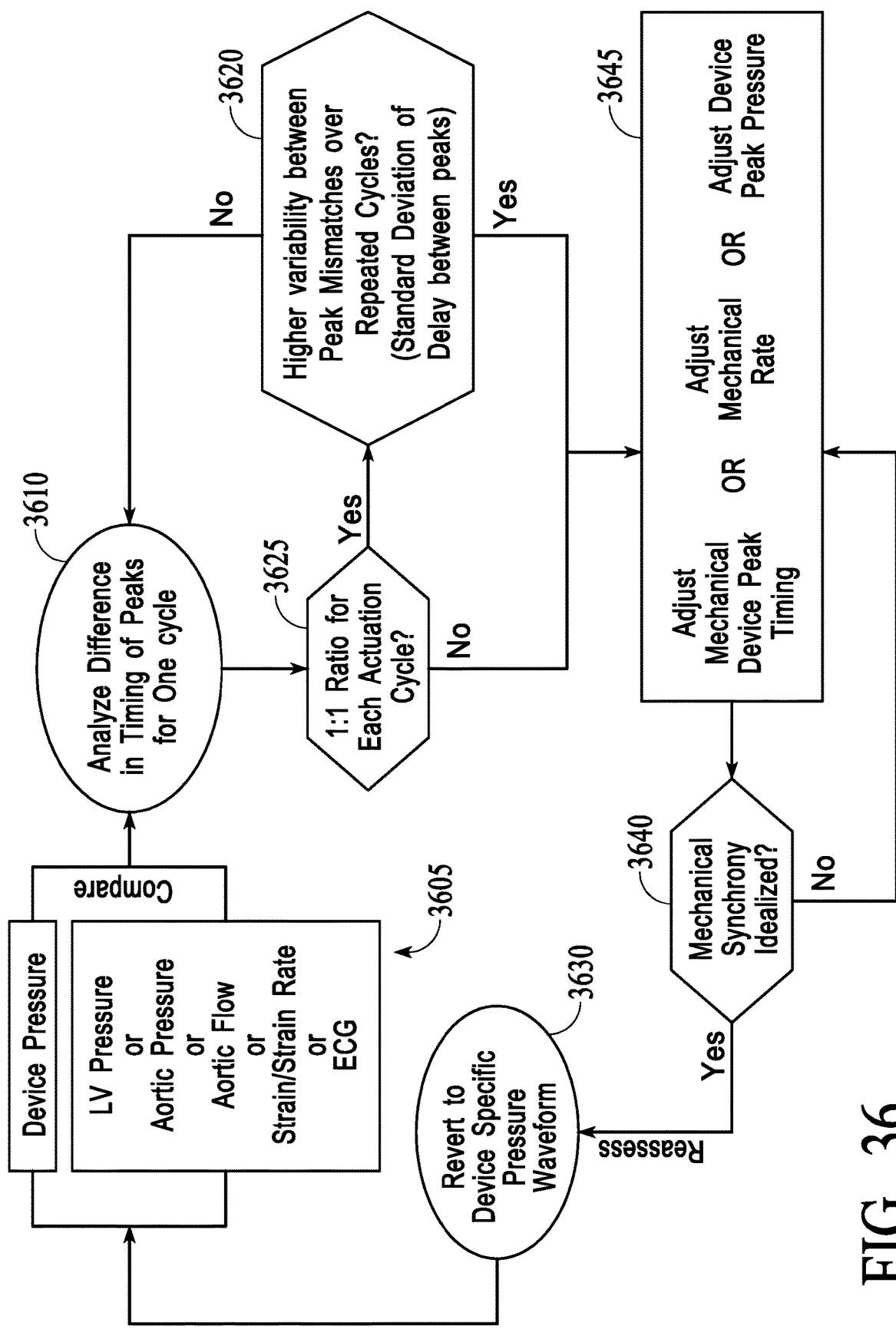
FIG. 36 illustrates a composite flowchart of device control with mechanical synchrony algorithm, according to an embodiment of the present disclosure.

FIGS. 34-36 pertain to the fourth order of control, i.e. the mechanical synchrony algorithm. Specifically, FIG. 34 illustrates a scheme for detecting higher variability between device pressure waveform and the physiologic waveform from a beating heart, because these two waveforms are compared for the functioning of the mechanical synchrony algorithm. A coordination index (CI) between the two waveforms can be calculated as follows:

$$CI = \sqrt{\frac{1}{N-1} \sum_{i=1}^{N} (d_i - \bar{d})^2} \quad \text{(Eq. 10)}$$

where $d_i$ is the time delay between peak heart signal (physiologic waveform) and device pressure waveform over one device pressure cycle; $\bar{d}$ is the average delay over N number of cycles, N is the number of consecutive cycles in recording (e.g., N can be any number greater than 3, but suggested N>10 or any other arbitrary number with increasing N leading to more accuracy). The coordination index (CI) is basically the standard deviation of delay between peaks.

FIG. 35 illustrates identification of the cycles featuring loss of ventricular capture, as part the mechanical synchrony algorithm. Loss of ventricular capture occurs when number of peaks from the heart signal is more than 1 (e.g., $H_1$ and $H_2$) and the time between the two adjacent peaks is more than a certain percentage of the length of the device pressure cycle, e.g., >10% of the cycle length with less cycle length indicating more synchrony.

FIG. 36 illustrates a composite flowchart of device control with mechanical synchrony algorithm, according to an embodiment of the present disclosure. The physiologic waveform and the device pressure waveforms are compared at 3605 and the difference in timing of peaks are analyzed at 3610 (as shown in FIG. 34). If at 3625 it is determined that each physiologic peak is matched with a device pressure peak in one cycle, then the match (or lack thereof) is assessed over multiple cycles (at 3620). If higher variability between peak mismatches are seen over repeated cycles, then at 3645, a corrective measure is taken, e.g., mechanical device peak timing is adjusted, or mechanical pacing rate is adjusted or device peak pressure is adjusted. If one or more of these corrective actions idealizes mechanical synchrony at 3640, then the device-specific pressure waveform is achieved (at 3630). If mechanical synchrony is not idealized, then the adjustments at 3645 are repeated. It is to be noted that the loss of ventricular capture, as described with respect to FIG. 35, can be detected at 3625, and can be corrected by taking any of the corrective measures discussed at 3645.

Figure 37:
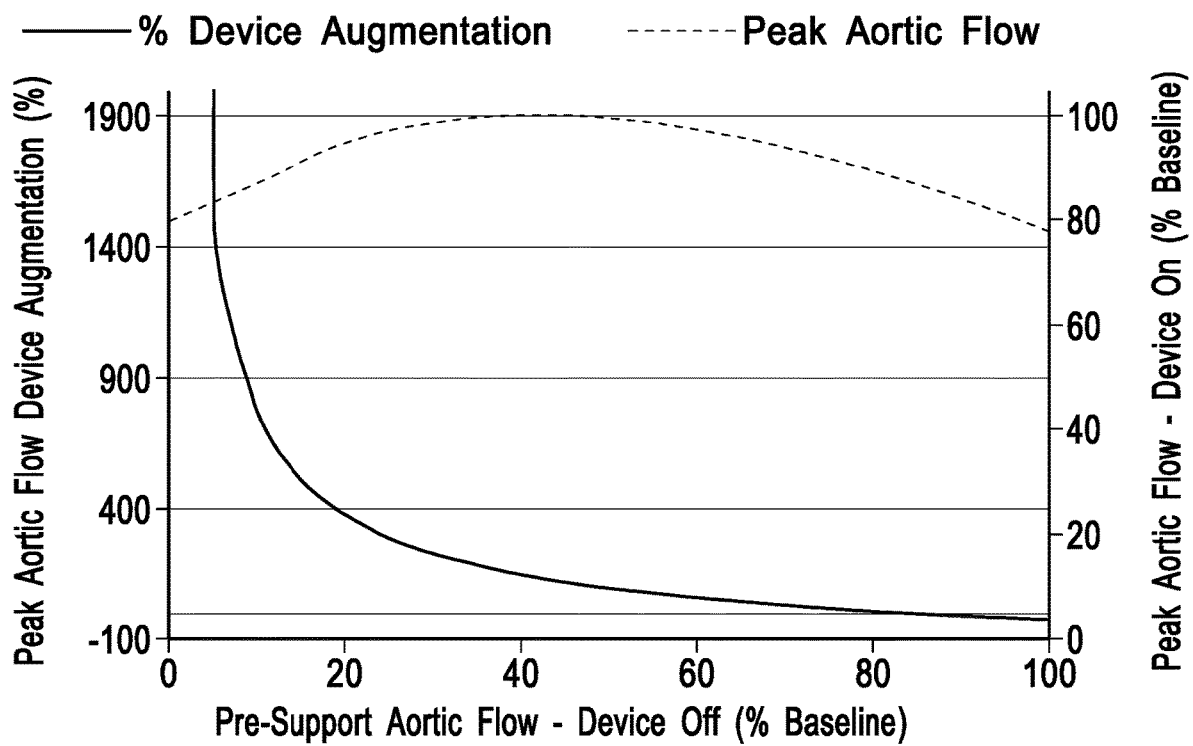
FIG. 37 illustrates target device augmentation of peak arterial (such as, aortic) flow relative to pre-support values, according to an embodiment of the present disclosure.
Figure 38:
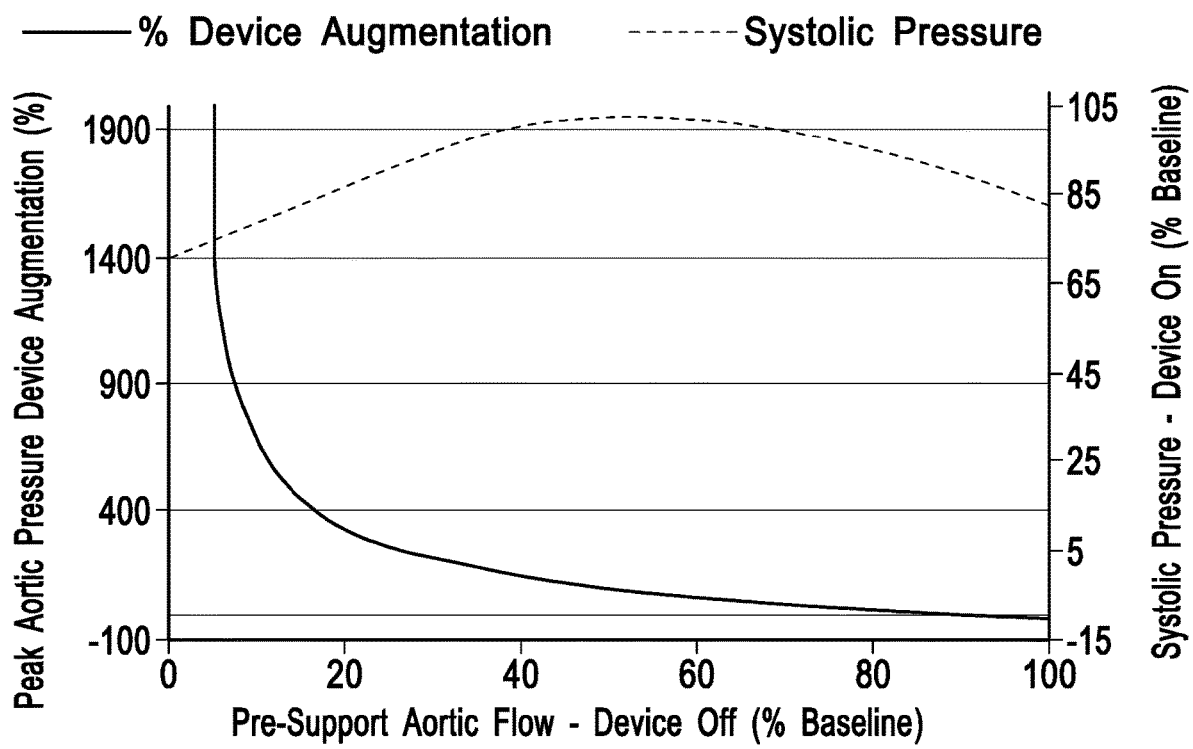
FIG. 38 illustrates target device augmentation of peak arterial (such as, aortic) pressure relative to pre-support values, according to an embodiment of the present disclosure.
Figure 39:
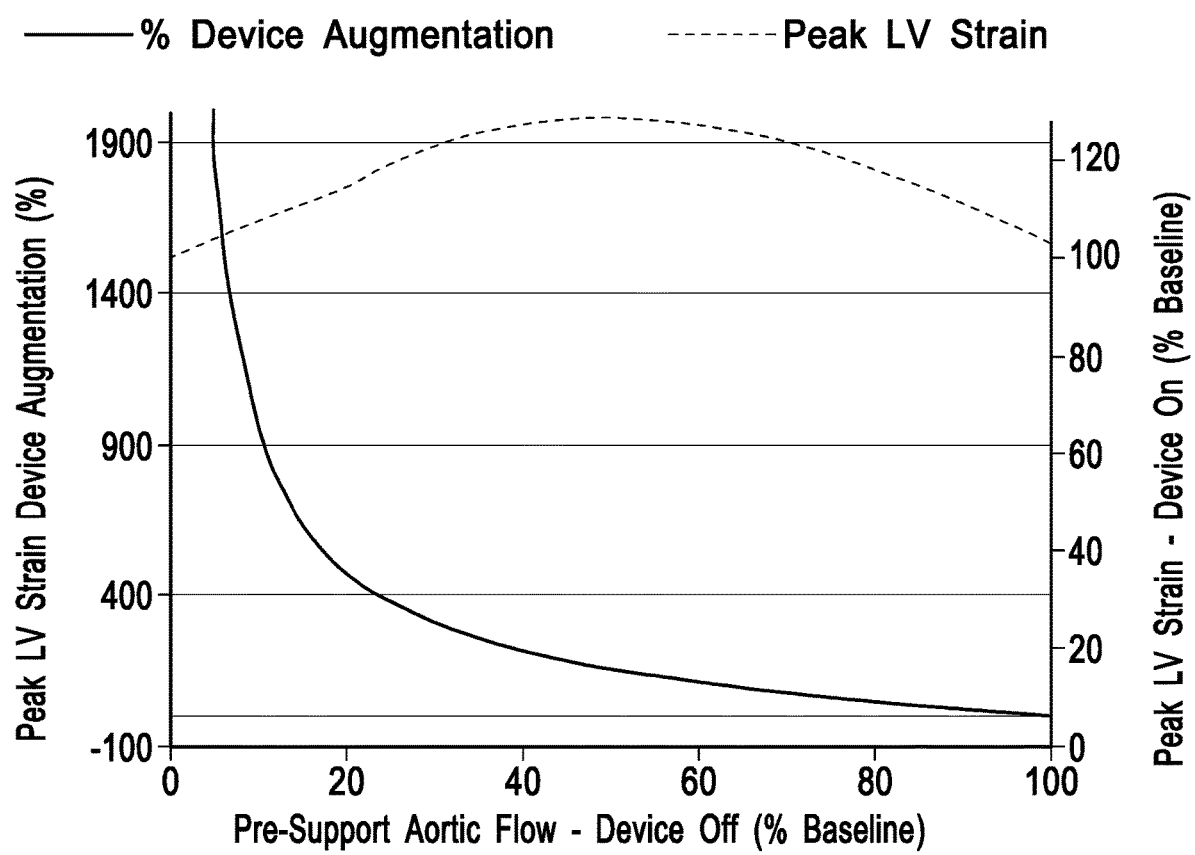
FIG. 39 illustrates target device augmentation of peak value of heart strain relative to pre-support values, according to an embodiment of the present disclosure.

FIGS. 37-39 illustrate the effectiveness of the cardiac device support in terms of peak arterial (e.g., aortic) flow/pressure augmentation, which can be targeted according to varying degrees of heart failure. These three figures have the x-axis showing pre-support aortic flow (as a percentage of baseline aortic flow), i.e. when the pump is off. On the extreme left of the x-axis show an aortic flow of zero, i.e. the heart is arrested and cannot pump at all. On the extreme right of the x-axis, the aortic flow is restored to 100% of its baseline capacity, i.e. with the support of the device, the heart's baseline function is restored.

Specifically, FIG. 37 illustrates anticipated device augmentation (in percentage, as shown by the solid curve) of peak aortic flow relative to pre-support values using relevant pumps acting on varying degrees of heart function for first order control. In conditions of normal heart function (far right on x-axis), there is little augmentation and in fact the aortic flow may actually fall below baseline as the device cannot improve flow above normal. Note that at approximately 60% (or other predetermined threshold percentage) of normal baseline function, the device can begin augmenting aortic flow significantly which rises substantially as heart function continues to decline. As heart function decline below 20% (or other predetermined threshold percentage), augmentation of aortic flow rises exponentially. The dashed curve representing target peak aortic flow contacts the 0 point of the pre-support aortic flow at the far left of the x-axis, which would be complete cardiac arrest. Note that target peak aortic flow generated by such devices are approximately 80-90% (or other predetermined threshold percentage) during arrest. These curves illustrate in particular that at times of "weaning" where device support is aiding a heart with substantial function, target control profiles will need further modification as they would be correlated with hemodynamic results to ensure that the device is actually aiding the heart.

FIG. 38 illustrates anticipated percentage of device augmentation (Solid curve) of peak aortic pressure relative to pre-support values using existing relevant devices. The degree of aortic pressure augmentation can be "targeted" with respect to varying degrees of heart failure for second order control. Note that the pre-support aortic flow as percentage of baseline is shown along the x- or horizontal axis. In conditions of normal heart function (far right on x-axis) there is little augmentation and in fact the aortic flow may actually fall below baseline as the device can not improve flow above normal. Note that at approximately 60% (or other predetermined threshold percentage) normal function, these device can begin augmenting aortic flow significantly which rises substantially as heart function continues to decline. As heart function decline below 20% (or other predetermined threshold percentage), augmentation of aortic pressure rises exponentially. The dashed curve representing systolic pressure contacts the 0 point on the far left of the x-axis, which would be complete cardiac arrest. Note that targeted systolic pressure generated by such devices are approximately 70% (or other predetermined threshold percentage) during arrest. These curves illustrate in particular that at times of "weaning" where device support is aiding a heart with substantial function, target control profiles will need further modification as they would be correlated with hemodynamic results to ensure that the device is actually aiding the heart.

FIG. 39 illustrates anticipated percent device augmentation (solid curve) of peak value of heart strain relative to pre-support values using existing cardiac support devices. The degree of peak LV strain can be "targeted" with respect to varying degrees of heart failure for third order control. Note that the pre-support aortic flow as percentage of baseline is shown along the x- or horizontal axis. In conditions of normal heart function (far right on x-axis) there is little augmentation and in fact the aortic flow may actually fall below baseline as the device can not improve flow above normal. Note that at approximately 60% (or other predetermined threshold percentage) normal function, these devices can begin augmenting aortic flow which rises substantially as heart function continues to decline. As heart function decline below a certain predetermined percentage, e.g., 20%, augmentation of aortic flow rises exponentially. The dashed curve representing peak LV strain contacts the 0 point of the x-axis at far left, which would be complete cardiac arrest. Note that target peak LV strain generated by such devices are approximately 95 to 110% baseline during arrest. These curves illustrate in particular that at times of "weaning" where device support is aiding a heart with substantial function, target control profiles would need further modification as they would be correlated with hemodynamic results to ensure that the device is actually aiding the heart.

In the foregoing specification, implementations of the disclosure have been described with reference to specific example implementations thereof. It will be evident that various modifications may be made thereto without departing from the broader spirit and scope of implementations of the disclosure as set forth in the following claims. The specification and drawings are, accordingly, to be regarded in an illustrative sense rather than a restrictive sense. Additionally, the directional terms, e.g., "top", "bottom" etc. do not restrict the scope of the disclosure to any fixed orientation, but encompasses various permutations and combinations of orientations.

What is claimed is:

1. A method of regulating a pump to support a partially or fully dysfunctional heart wherein the pump imparts external force to an outer surface of the heart, the method comprising:

obtaining an initial value for a selected dimension of the heart, wherein the selected dimension is a total volume occupied by an entire portion of the heart just below atrio-ventricular valves including the heart's ventricular walls and ventricular chambers as well as blood contained therein at the end of diastole, and wherein the selected dimension is incorporated in an algorithm that regulates the pump, wherein the pump is regulated by selecting one or more of the following control mechanisms: controlling a volume of flow of a fluid in the pump, controlling a pressure of fluid in the pump, and, controlling a function of the pump based on one or both of a strain and a strain rate in a wall of the heart;

measuring or estimating periodic changes in the selected dimension of the heart to update the algorithm; and imparting external force by the pump to the outer surface of the heart based on the algorithm.

2. The method of claim 1, wherein a computer processor calculates one or more parameters of the selected control mechanism in order to match a target profile corresponding to the inti value of the total volume occupied by the entire portion of the heart just below the atrio-ventricular valves including the heart's ventricular walls and ventricular chambers as well as blood contained therein at the end of diastole.

3. The method of claim 2, wherein a set of target profiles corresponds to one or both of a systolic and a diastolic phase.

4. The method of claim 1, wherein the pump operates in an actuation mode in which a substantive portion of the heart's pump function is imparted by the pump coupled with a drive system, while the heart itself is fully or severely compromised to perform a pump function.

5. The method of claim 1, wherein the pump operates in an assist mode in which the pump coupled with a drive system augments the heart's pump function, while the heart itself is capable of performing a predetermined threshold percentage of a normal pump function.

6. The method of claim 1, wherein each selected control mechanism can operate independent of another control mechanism that is available.

7. A method of regulating a pump to support a partially dysfunctional heart, wherein the pump imparts external force to an outer surface of the heart, the method comprising:
obtaining an initial value for a selected dimension of the heart, wherein the selected dimension is a total volume occupied by an entire portion of the heart just below atrio-ventricular valves including the heart's ventricular walls and ventricular chambers as well as blood contained therein at the end of diastole, wherein the selected dimension is incorporated in an algorithm that regulates the pump, wherein the pump is regulated by selecting one or more of the following control mechanisms: controlling a volume of flow of a fluid in the pump, controlling a pressure of fluid in the pump, and, controlling a function of the pump based on one or both of a strain and a strain rate in a wall of the heart;
measuring or estimating: periodic changes in a native contraction parameter of the heart;
adjusting a parameter of the pump in the algorithm that corresponds to the native contraction parameter of the heart to mechanically synchronize the parameter of the pump with the native contraction parameter of the heart such that a first waveform physiologically generated by the heart substantially conforms with a second waveform generated by the pump; and
imparting external force by the pump to the outer surface of the heart based on the algorithm.

8. The method of claim 7, wherein the first waveform generated by the heart represents time variation of a physiologic quantity, and the second waveform generated by the pump represents time variation of the parameter of the pump.

9. The method of claim 8, the physiologic quantity is selected from the following: ventricle pressure, arterial pressure, arterial flow, one or both of a strain and a strain rate in a wall of the heart, or, electrocardiogram.

10. The method of claim 9, wherein adjusting the parameter of the pump comprises adjusting one or more of the following: timing of a peak of the second waveform, mechanical actuation rate of the pump, or, peak intensity of the parameter of the pump.

11. The method of claim 8, wherein the method comprises:
calculating, by a computer processor executing the algorithm, a coordination index (CI), for detecting a degree of mismatch between the first waveform and the second waveform.

12. The method of claim 11, wherein the coordination index (CI) is calculated according to the following standard deviation formula:

$$CI = \sqrt{\frac{1}{N-1}\sum_{i=1}^{N}(d_i - \bar{d})^2}$$

wherein $d_i$ is a time delay between a peak of the first waveform and a corresponding peak of the second waveform over one cycle of variation of the parameter of the pump;
$\bar{d}$ is an average delay over N number of cycles;
N is the number of consecutive cycles in a recorded trace of the first and the second waveforms.

13. The method of claim 12, where N is able to be selected by a user depending on a desired accuracy.

14. The method of claim 8, further comprising:
detecting loss of ventricular capture by the algorithm.

15. The method of claim 14, wherein detecting the loss of ventricular capture comprises:
counting a number of peaks of the first waveform within a length of one cycle of the second waveform;
responsive to counting more than one peaks of the first waveform within a length of one cycle of the second waveform, measuring time between two adjacent peaks of the first waveform generated by the heart;
determining, by a computer processor executing the algorithm, whether the measured time between the two adjacent peaks of the first waveform exceeds a predetermined threshold percentage of the length of one cycle of the second waveform; and
deciding, based on the determination, whether the loss of ventricular capture has occurred.

16. A method of regulating a pump to support a partially or fully dysfunctional heart, wherein the pump imparts external force to an outer surface of the heart, the method comprising:
obtaining an initial value for a selected dimension of the heart, wherein the selected dimension is a total volume occupied by an entire portion of the heart just below atrio-ventricular valves including the heart's ventricular walls and ventricular chambers as well as blood contained therein at the end of diastole, wherein the selected dimension is incorporated in an algorithm that regulates the pump, wherein the pump is regulated by selecting one or more of the following control mechanisms: controlling a volume of flow of a fluid in the pump, controlling a pressure of fluid in the pump, and, controlling a function of the pump based on one or both of a strain and a strain rate in a wall of the heart, wherein the algorithm has a mechanical synchrony component;
measuring or estimating periodic changes in the selected dimension of the heart to update the algorithm;
responsive to determining that the heart is partially functional, measuring periodic changes in a native contraction parameter of the heart;
adjusting a parameter of the pump in the mechanical synchrony component of the algorithm that corresponds to the native contraction parameter of the heart to mechanically synchronize the parameter of the pump with the native contraction parameter of the heart such that a first waveform physiologically generated by the heart substantially conforms with a second waveform generated by the pump; and imparting external force by the pump to the outer surface of the heart based on the algorithm.

* * * * *